(12) United States Patent
Armelin Diggroc et al.

(10) Patent No.: US 11,067,528 B2
(45) Date of Patent: Jul. 20, 2021

(54) ELECTRO-CHEMICAL SENSOR AND COATING METHOD, PRODUCTION METHOD AND CORRESPONDING USES

(71) Applicant: UNIVERSITAT POLITÈCNICA DE CATALUNYA, Barcelona (ES)

(72) Inventors: Elaine Armelin Diggroc, Barcelona (ES); Georgina Fabregat Jové, Barcelona (ES); Jordi Llorca Pique, Barcelona (ES); Carlos Alemán Llansó, Barcelona (ES)

(73) Assignee: UNIVERSITAT POLITÈCNICA DE CATALUNYA, Barcelona (ES)

( * ) Notice: Subject to any disclaimer, the term of this patent is extended or adjusted under 35 U.S.C. 154(b) by 0 days.

(21) Appl. No.: 16/065,080

(22) PCT Filed: Nov. 22, 2016

(86) PCT No.: PCT/ES2016/070832
§ 371 (c)(1),
(2) Date: Jun. 21, 2018

(87) PCT Pub. No.: WO2017/109244
PCT Pub. Date: Jun. 29, 2017

(65) Prior Publication Data
US 2019/0004001 A1    Jan. 3, 2019

(30) Foreign Application Priority Data
Dec. 22, 2015   (ES) ................ ES201531868

(51) Int. Cl.
*G01N 27/30* (2006.01)
*G01N 27/12* (2006.01)
(Continued)

(52) U.S. Cl.
CPC .............. *G01N 27/30* (2013.01); *B82Y 30/00* (2013.01); *G01N 27/126* (2013.01); *G01N 27/26* (2013.01);
(Continued)

(58) Field of Classification Search
CPC ... G01N 33/9413; G01N 27/308; G01N 27/30
See application file for complete search history.

(56) References Cited

U.S. PATENT DOCUMENTS 6,863,800 B2    3/2005  Karinka et al.
7,276,283 B2 *  10/2007 Denes .................... A61K 48/00
                                                    428/403
(Continued)

FOREIGN PATENT DOCUMENTS

CN    100424180 C    10/2008
CN    103487484 A    1/2014
(Continued)

OTHER PUBLICATIONS

E. Luais, Preparation and modification of carbon nanotubes electrodes by cold plasmas processes toward the preparation of amperometric biosensor, 55 Electrochimica Acta, 2010, p. 7916-22. (Year: 2010).*
(Continued)

*Primary Examiner* — Luan V Van
*Assistant Examiner* — Caitlyn Mingyun Sun
(74) *Attorney, Agent, or Firm* — Seed IP Law Group LLP

(57) ABSTRACT

The invention relates to an electro-chemical sensor and coating method, production method and corresponding uses. The coating method of an electro-chemical sensor comprises the following steps: coating a carbon-rich substrate, with a carbon content greater than or equal to 0 wt. % in relation to the total weight of the substrate, and with an organic polymer; and applying a cold plasma treatment to said coating. This method permits the production of electro-
(Continued)

chemical sensors with a carbon-rich substrate, with a carbon content greater or equal to 50 wt. % in relation to the total weight of the substrate, and a modified organic polymer coating. These new sensors are suitable for the detection of, inter alia, dopamine, glucose, uric acid and ascorbic acid.

12 Claims, 16 Drawing Sheets

(51) Int. Cl.
    *G01N 27/327* (2006.01)
    *B82Y 30/00* (2011.01)
    *G01N 33/50* (2006.01)
    *G01N 27/26* (2006.01)
    *C01B 32/158* (2017.01)

(52) U.S. Cl.
    CPC ......... *G01N 27/308* (2013.01); *G01N 27/327* (2013.01); *G01N 33/50* (2013.01); *C01B 32/158* (2017.08)

(56) References Cited

U.S. PATENT DOCUMENTS

| | | |
|---|---|---|
| 7,797,825 B2 | 9/2010 | Say et al. |
| 2008/0164142 A1 | 7/2008 | Alvarez-Icaza et al. |
| 2019/0231573 A1 | 8/2019 | Lugrís Armesto et al. |

FOREIGN PATENT DOCUMENTS

| | | |
|---|---|---|
| EP | 1 916 309 A2 | 4/2008 |
| EP | 1 916 309 A3 | 11/2010 |
| JP | 62-127533 A | 6/1987 |

OTHER PUBLICATIONS

G. Fabregat, A rational design for the selective detection of dopamine using conducting polymers, Phys. Chem. Chem. Phys. 2014 (16) p. 7850-61. (Year: 2014).*
Dai et al., "Modified Carbon Nanoball on Electrode Surface Using Plasma in Enzyme-Based Biofuel Cells," *Energy Procedia* 14:1804-1810, 2012.
Fabregat et al., "A rational design for the selective detection of dopamine using conducting polymers," *Phys. Chem. Chem. Phys.* 16:7850-7861, 2014.
Liu et al., "Electromechanical detection of dopamine in the presence of ascorbic acid using PVP/graphene modified electrodes," *Talanta* 97:557-562, 2012.
Luais et al., "Preparation and modification of carbon nanotubes electrodes by cold plasmas processes toward the preparation of amperometric biosensors," *Electrochimica Acta* 55:7916-7922, 2010.
Maekawa et al., "Use of a Surface-Modified Poly(dimethylsiloxane) Layer for the Preparation of Amperometric Glucose Sensor," *Electrochemistry* 77(4):319-321, 2009.
Mortensen et al., "Modification of Glassy Carbon Surfaces by Atmospheric Pressure Cold Plasma Torch," *Japanese Journal of Applied Physics* 45(10B):8506-8511, 2006.
Wu et al., "A dopamine sensor based on a methoxypolyethylene glycol polymer covalently modified glassy carbon electrode," *Analyst* 138:1204-1211, 2013.
Zhao et al., "Carbon Nanotube Nanoweb-Bioelectrode for Highly Selective Dopamine Sensing," *ACS Applied Materials & Interfaces* 4:44-48, 2012.
Buendia et al., "Plasma-treated polyethylene as electrochemical mediator for enzymatic glucose sensors: Toward bifunctional glucose and dopamine sensors," *Plasma Process Polym.* 15(1):1-10, 2018.

* cited by examiner

DRAWINGS

ELECTRO-CHEMICAL SENSOR AND COATING METHOD, PRODUCTION METHOD AND CORRESPONDING USES

FIELD OF THE INVENTION

The invention relates to an electrochemical sensor for the detection of various organic substances, such as, for example, dopamine, glucose, uric acid, and/or ascorbic acid, in various body fluids, such as, for example, in blood and/or urine.

The invention also relates to an electrochemical sensor coating method according to the invention, to a production method for producing an electrochemical sensor according to the invention, and to the various uses thereof.

STATE OF THE ART

Dopamine (DA), a member of the catecholamine family, acts as an important neurotransmitter in the central nervous system of mammals, modulating vital functions such as voluntary movement. It is related to cognitive and motor functions. In patients with Parkinson's disease, the DA-releasing (dopaminergic) neurons in the central nervous system are dysfunctional or dying, causing a lack of dopamine in the target territories, which leads to impaired motor functions.

Electrochemical techniques have become predominant among the potential methods developed in the past decades for the detection of DA as a result of their significant advantages, such as a quick response, low cost, and high sensitivity. However, there are some limitations for measuring DA in physiological conditions by means of conventional electrochemical methods. The main limitations are related to selectivity for other species coexisting in the organism, such as ascorbic acid (AA) and uric acid (UA), which oxidize at almost the same potential. Likewise, the detection of very low DA levels (10 nM-10 µM) represents a challenge for sensitivity. Recent publications have reported the existence of various strategies using, among others, nanocomposites, graphene, conductive polymers (CP), catalytic nanoparticles, or carbon nanotubes, to solve said problems. Nevertheless, the development of these electrochemical sensors make it necessary to have a large number of production steps, given that the application of the aforementioned compounds usually requires functionalization, nano-object incorporation, nanocomposition processing, multi-step synthesis processes, etc.

There is therefore the need to develop new electrochemical sensors for the detection of various organic substances, particularly dopamine, glucose, uric acid, and/or ascorbic acid, in various body fluids, such as, for example, in blood and/or urine.

BRIEF DESCRIPTION OF THE INVENTION

The object of the invention is to overcome these drawbacks. This objective is achieved by means of an electro-chemical sensor coating method, characterized in that it comprises the steps of:
  coating a carbon-rich substrate, with a carbon content greater than or equal to 50% by weight with respect to the total weight of the substrate, with an organic polymer,
  applying a cold plasma treatment to said coating.

The plasma preferably is an atmospheric plasma, a vacuum plasma, or a corona energy plasma comprised between 0.1 mJ/cm$^2$ and 100 J/cm$^2$ in an atmosphere with oxygen, or nitrogen, or another inert gas.

Advantageously, the organic polymer is a non-electrochemically active polymer, and preferably a polymer of the group consisting of polyethylene, poly(tetramethylene-succinate), polypropylene, polyvinylpyrrolidone, polyethylene oxide, poly(4-vinylphenol), polycaprolactone, polyamide PA 66, polystyrene, polyacrylic acid, and cellulose.

Alternatively, the organic polymer can be advantageously an electrochemically active polymer (i.e., a polymer with conjugated bonds or a conductive polymer), and preferably a polymer of the group consisting of poly(3,4-ethylenedioxythiophene) and poly(N-cyanoethylpyrrole).

Preferably, the plasma application time is more than 1 s (and advantageously more than 15 s) and/or less than 120 s.

Advantageously, the carbon-rich substrate is of a material from the group consisting of graphite, glassy carbon, nanostructured carbons (preferably graphene or carbon nanotubes), and fullerenes.

Another object of the invention is a production method for producing an electrochemical sensor comprising a carbon-rich substrate with a carbon content greater than or equal to 50% by weight with respect to the total weight of the substrate, characterized in that it includes a step of performing surface treatment on said substrate by means of plasma.

Another object of the invention is a production method for producing an electrochemical sensor comprising a carbon-rich substrate with a carbon content greater than or equal to 50% by weight with respect to the total weight of the substrate, characterized in that it comprises a step of coating according to the invention.

Another object of the invention is an electrochemical sensor, characterized in that it comprises a carbon-rich substrate with a carbon content greater than or equal to 50% by weight with respect to the total weight of the substrate, and an organic modified polymer coating, where the modified polymer coating can be obtained by means of a method according to the invention.

Another object of the invention is the various uses thereof:
  the use of a method according to the invention for producing an electrochemical sensor. The sensor is preferably for the detection of dopamine, glucose, uric acid, and/or ascorbic acid.
  the use of a sensor according to the invention for the detection of dopamine, glucose, uric acid, and/or ascorbic acid.

BRIEF DESCRIPTION OF THE DRAWINGS

Other advantages and features of the invention can be seen from the following description in which preferred embodiments of the invention are described in a non-limiting manner in reference to the attached drawings. The drawing show.

DETAILED DESCRIPTION OF SEVERAL EMBODIMENTS OF THE INVENTION

Part One

One of the surprising results of the present invention is the application of a cold plasma (plasma in which the ions and electrons are not in thermal equilibrium) as a very simple and effective technique for preparing electrochemical DA (dopamine) sensors. The experiments were initially performed using two conductive polymers, specifically PEDOT and PNCPy, which were deposited on bare GCE electrodes by means of chronoamperometry. The response of the two CPs with respect to DA was completely different. The selective and simultaneous detection of DA, UA (uric acid), and AA (ascorbic acid) using PNCPy is difficult because the oxidation peaks of each of these organic substances are weak and partially overlap one another, whereas, in contrast, the oxidation peaks are well resolved when PEDOT-coated electrodes are used. The behavior of PNMPy improves when the film is covered with gold nanoparticles (AuNPs), which demonstrates the electrocatalytic activity that the latter promote. In contrast, the properties of the PEDOT electrodes for the selective detection of DA remain virtually unchanged after the incorporation of AuNPs.

Both the PEDOT films and the PNCPy films generated by anodic polymerization on a CGE electrode were modified by means of applying cold plasma surface treatment (corona plasma in ambient atmosphere at about 0.5 J/cm$^2$ for 2 minutes).

DA, UA, and AA detection assays (100 μM each) were carried out by means of cyclic voltammetry (CV) using a glass cell containing 10 ml of 0.1 M PBS (phosphate-buffered saline solution) at room temperature. FIGS. 1 to 5 show the voltammetric response of PNCPy- and PEDOT-coated GCEs not treated and treated with plasma. The voltammograms recorded using bare GCEs have been included for comparative purposes. Although plasma treatment causes a significant reduction in anodic peak intensity at 0.70 V for all the systems, it must be indicated that this effect is relatively small for anodic intensities associated with the oxidation of the three analytes. Furthermore, as can be seen, both the electrode with PEDOT and the electrode with PNCPy treated with plasma are capable of selectively detecting DA, UA, and AA oxidation, whereas PNCPy that is not treated is not capable of selectively distinguishing one from the other. As regards the bare GCE, it is not capable of selectively detecting the presence of AA in the mixture, regardless of the plasma treatment. In the case of electrodes treated with plasma, small or even imperceptible peaks have been identified in some voltammograms (marked with arrows in FIG. 1). These peaks, which are shifted with respect to the identified oxidation peaks, have been associated with the oxidation processes of AA (PNCPy, PEDOT, and bare GCE) or UA (only PNCPy) by means of non-predominant reactive species created during cold plasma treatment.

Figure 1:
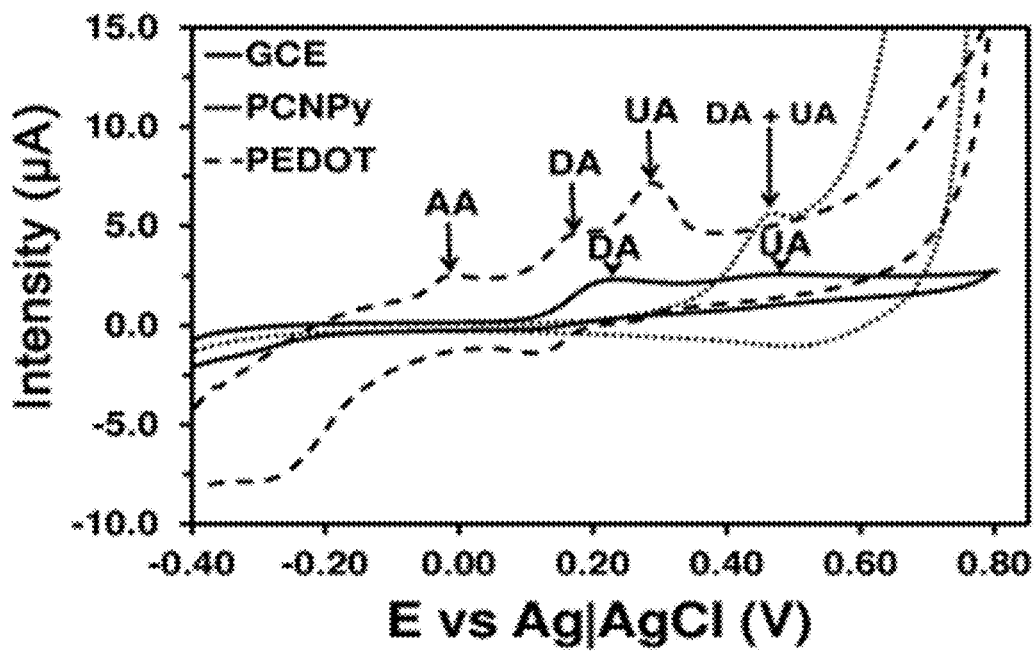
FIG. 1. Control voltammograms of 100 µM DA, 100 µM UA, and 100 µM AA in a 0.1 M phosphate-buffered saline (PBS) solution recorded using untreated substrates (electrodes): glassy carbon (GCE) bare GCE, poly(3,4-ethylene-dioxythiophene)-coated GCE (PEDOT), and poly(N-cyanoethylpyrrole)-coated GCE (PNCPy).
Figure 2:
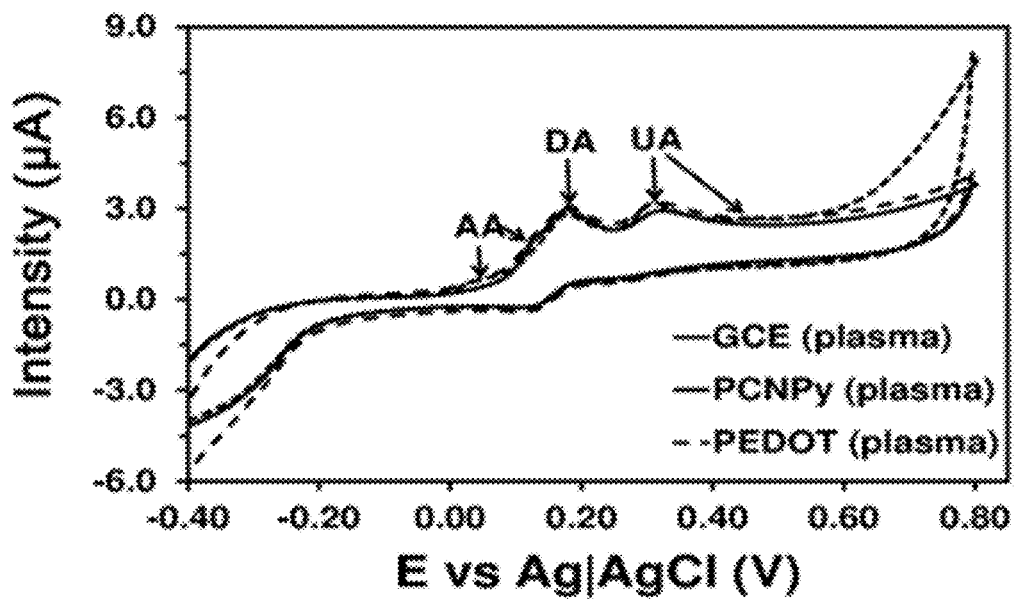
FIG. 2. Control voltammograms of 100 µM DA, 100 µM UA, and 100 µM AA in a 0.1 M phosphate buffer (PBS) solution recorded using plasma-air-treated substrates (electrodes): bare GCE, poly(3,4-ethylenedioxythiophene)-coated GCE (PEDOT), and poly(N-cyanoethylpyrrole)-coated GCE (PNCPy).

FIGS. 1 and 2 show the control voltammograms of 100 μM DA, 100 μM UA, and 100 μM AA in 0.1 M PBS for bare GCE, PEDOT-coated GCE, and PNMPy-coated GCE. The arrows indicate oxidation processes. Scan rate: 100 mV/s. Initial and final potentials: −0.40 V; Reversal potential: +0.80 V.

Figure 3:
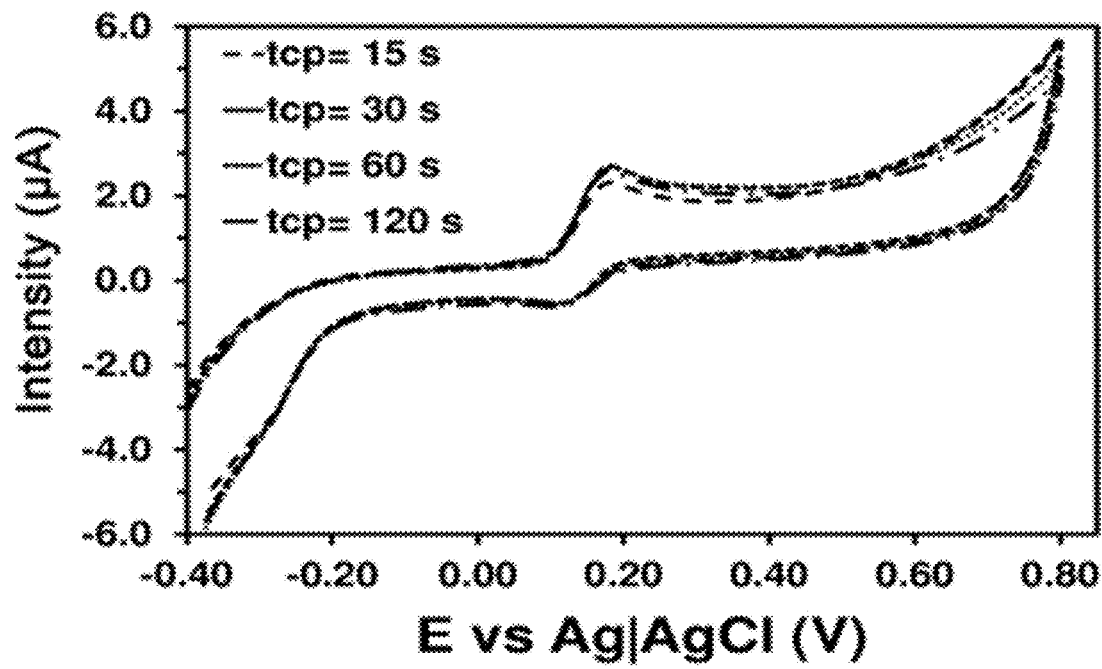
FIG. 3. Control voltammograms of 100 μM DA in 0.1 M PBS collected in PEDOT-coated GCE treated with cold plasma prepared using different plasma-air application times ($t_{cp}$).

An important question is the influence the time during which plasma power ($t_{cp}$) is applied has on the effective detection of DA. For this purpose, PEDOT-coated GCEs were treated considering different $t_{cp}$ values (i.e., from 15 to 120 s). FIG. 3 compares the voltammograms of 100 μM DA in 0.1 M PBS with these treated electrodes. As can be seen, $t_{cp}$ has zero influence on oxidation peak potential (E=0.176 V in all the cases). Similarly, $t_{cp}$ has very little influence on anodic peak intensity ($i_p$). This is reflected in FIG. 5 which depicts the mean of the $i_p$ taking into account four different samples, with respect to $t_{cp}$. Therefore, $i_p$ increases from 1.50 to 1.63 μA when $t_{cp}$ increases from 15 to 120 s. According to these results, $t_{cp}$ is not a decisive factor for the detection process once exceeding 15 s.

Figure 4:
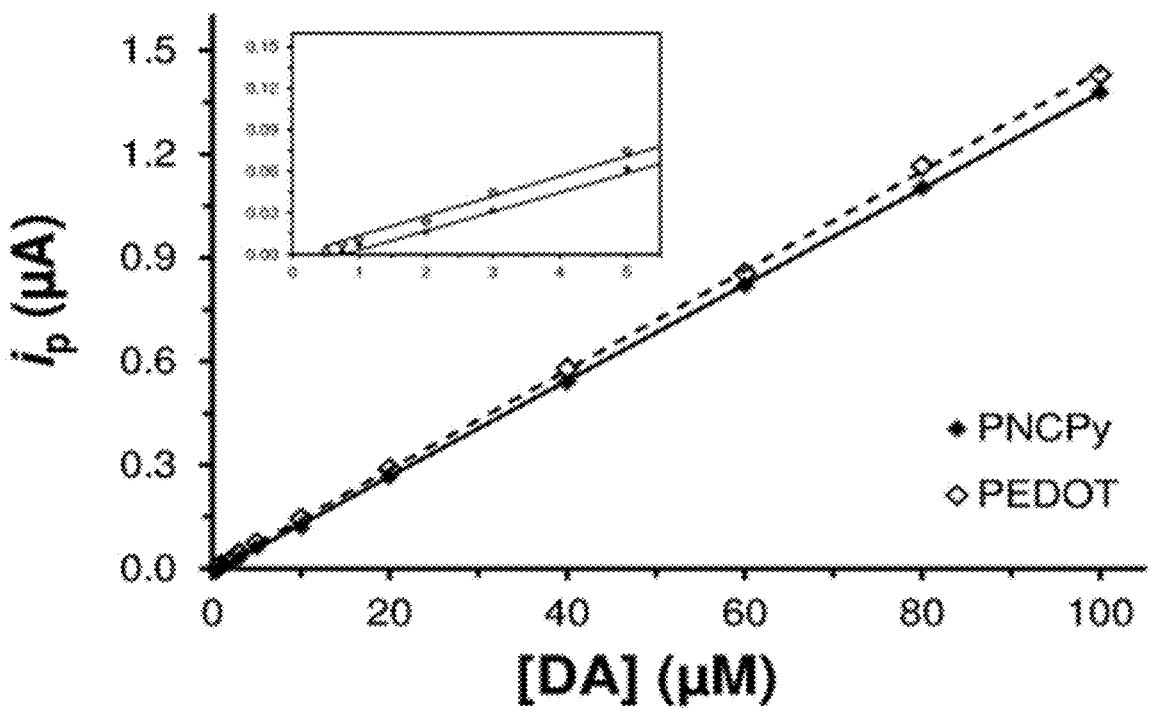
FIG. 4. Determination of the DA detection limit of PEDOT- and PNCPy-coated GCEs with plasma-air treatment.
Figure 5:
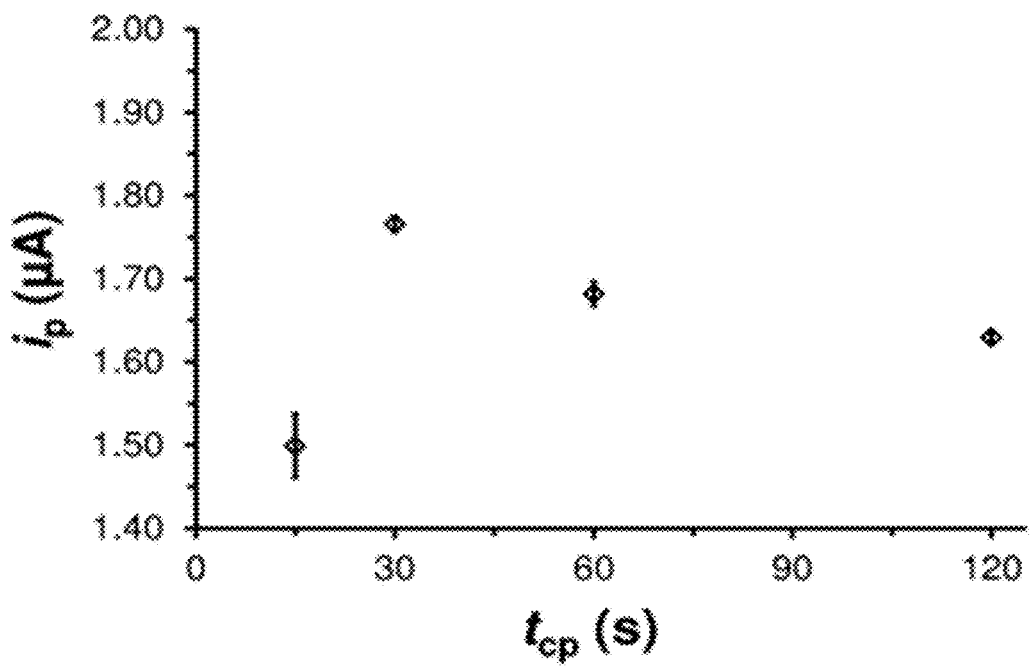
FIG. 5. Variation of anodic peak intensity ($i_p$) in PEDOT-coated GCEs with cold plasma treatment with respect to plasma application time ($t_{cp}$).

FIG. 4 shows the determination of the DA detection limit (in the absence of UA, and AA) of PEDOT- and PNCPy-coated GCEs with cold plasma treatment by means of CV using a scan rate of 50 mV·s$^{-1}$. The results were derived from the standard addition of 10 μL of DA in 10 ml of 0.1 M PBS (i.e., a linear interval of 0.5 to 100 μM DA). The anodic peak intensity (ip) increases with the concentration of DA for the two electrodes. The detection limit, which was determined using a calibration curve for the concentration of DA comprised between 0.5 and 5 μM (box) was comprised between 140 and 750 nM for PEDOT and PNCPy, respectively. These values are significantly lower than those obtained for the untreated samples, and prove an improvement not of the resolution alone (particularly for PNCPy).

Experimental Methods:

Materials. 3,4-ethylenedioxythiophene (EDOT), N-(2-cyanoethyl)pyrrole (NCPy), acetonitrile, anhydrous salt lithium perchlorate (LiClO$_4$), DA hydrochloride (3-hydroxytyramine hydrochloride), AA (L-configuration, crystalline), UA (crystalline) of analytical reagent grade. All chemicals acquired from the company Sigma Aldrich (Spain) were used without further purification. The 0.1 M phosphate buffer solution (PBS) with pH=7.4 was prepared as an electrolyte solution by mixing four stock solutions of NaCl, KCl, NaHPO$_4$, and KH$_2$PO$_4$. High-purity nitrogen was used for the de-aeration of the prepared aqueous solutions.

Conductive polymer synthesis. PEDOT and PNCPy films were prepared by means of chronoamperometry (CA) under a constant potential of 1.40 V using a two-compartment, three-electrode cell under nitrogen atmosphere (99.995% of purity) at 25° C. A bare glassy carbon electrode (GCE) with a diameter of 2 mm was used as the working electrode, whereas a AISI 316 steel sheet with a area of 1 cm$^2$ was used as the counter electrode. The surface of the glassy carbon electrode was polished with alumina powder and cleaned by means of ultrasonication before depositing the polymer. The reference electrode was an Ag|AgCl electrode containing a saturated aqueous KCl solution (E°=0.222 V vs. standard hydrogen electrode at 25° C.) which was connected with the working compartment through a saline bridge containing the electrolyte solution. All electrochemical experiments were performed in an AUTOLAB PGSTAT302N potentiostat-galvanostat (Ecochimie, The Netherlands) equipped with the ECD module for measuring very low current densities (100 μA-100 μA), which was connected with a computer controlled by means of the NOVA 1.6 software.

PEDOT and PNCPy films were obtained using 10 mM of a monomer solution in acetonitrile with 0.1 M of LiClO$_4$ and a polymerization period comprised between 6 and 10 s, respectively.

Cold plasma treatment. PEDOT- and PNCPy-coated GCEs were prepared with a corona discharge in ambient atmosphere using a BD-20AC from the company Electro-Technic Products. The BD-20AC works at a very high frequency in the MHz range, generating an electric field that is created around the electrode which is used for polymer surface treatment. The unit consists of a power control unit and a separate high-voltage handle. What differentiates it from other models is that it generates an adjustable high-voltage output comprised between 10,000 and 45,000 volts at a high frequency of 4.5 MHz. The polymers were treated using a spring tip wire electrode and a voltage of 45,000 volts at a high frequency of 4.5 MHz in all cases. After plasma treatment, the coated GCE electrodes were used for DA detection experiments within a period of 24 hours.

Electrochemical measurements for the detection of DA. Electromechanical detection was carried out by means of cyclic voltammetry (CV) using the Autolab PGSTAT302N equipment described above. All electrochemical experiments were carried out in a glass cell containing 10 ml of 0.1 M PBS (pH=7.4) at room temperature and equipped with saturated Ag|AgCl as the reference electrode and a platinum (Pt) wire as the counter electrode. Voltammograms were recorded in the potential interval comprised between −0.40 and 0.80 V at a scan rate of 50 mV·s$^{-1}$ unless another scan rate is explicitly specified. All the electrodes were in contact with the electrolyte solution for 5 minutes before CV measurements.

Part Two

Figure 6:
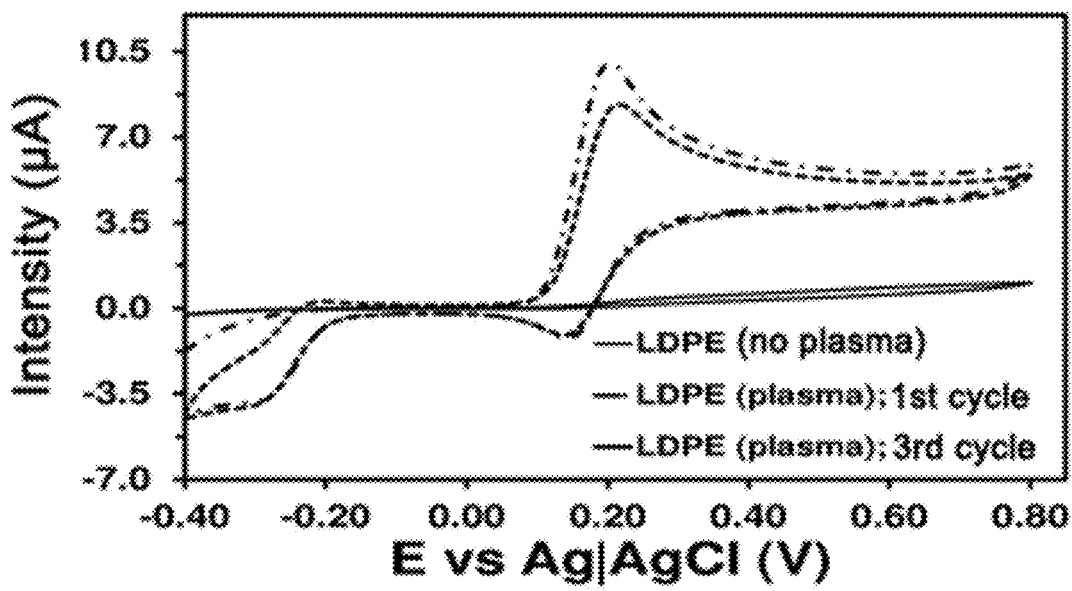
FIG. 6. Control voltammogram of 1 mM DA in 0.1 M PBS in low-density polyethylene (LDPE)-coated GCE with and without plasma-air treatment. The first and third cycle for the electrode that is treated with plasma-air is shown.

As a proof of concept, sensors made of GCEs coated with a very cost-effective and electrochemically inert polymer, i.e., low-density polyethylene, were produced and verified. Low-density polyethylene (LDPE) was deposited on the GCE by means of solution (34.4 mg of LDPE dissolved in 10 ml of dichlorobenzene at 95° C. by means of stirring for 4 hours). For the LDPE-coated GCE without cold plasma treatment, the cyclic voltammogram recorded in a 0.1 M PBS solution with 1 mM of DA does not provide any oxidation peak (FIG. 6) indicating that, as expected, LDPE is not able to detect said neurotransmitter. In contrast, the voltammogram recorded using an electrode produced in the same way, but applying a cold plasma treatment for 1 minute, shows a considerable potential at 0.20 V which corresponds to DA oxidation (FIG. 6). Considering that the concentration of DA estimated in the synapse is 1.6 mM, this result corroborates that efficient detectors can be produced by combining an organic matrix with a simple plasma-air treatment. Furthermore, this detector is very stable since it only decreases ~2 µA (FIG. 6) after three consecutive oxidation-reduction cycles (i.e., detection cycles).

FIG. 6 shows the control voltammogram of 1 mM DA in 0.1 M PBS in the LDPE-coated GCE. The voltammograms recorded using untreated electrodes (solid line) and electrodes treated with cold plasma (dash-dot: first detection cycle; dash-dash-dot: third detection cycle (Scan rate: 100 mV/s. Initial and final potentials: −0.40 V; Reversal potential: +0.80 V) As can be seen, LDPE-coated electrodes treated with a simple plasma-air for 1 minute are capable of detecting concentrations of DA similar to those estimated for the synapse for several cycles.

Figure 7:
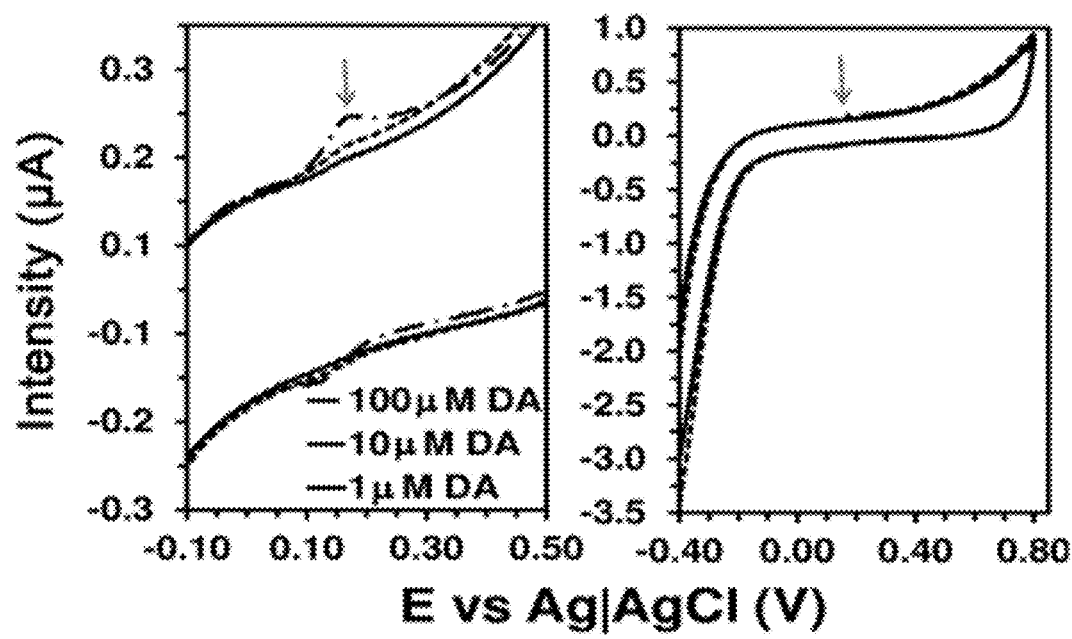
FIG. 7. Control voltammograms of 100, 10, and 1 μM DA in LPDE-coated GCEs treated with plasma-air. Right: Complete voltammograms; Left: Enlargement of the area associated with DA oxidation. In all the cases: scan rate: 100 mV/s; final and initial potentials: −0.40; Reversal potential: +0.80 V.

Additional assays were carried out with LDPE-coated GCEs treated with cold plasma using concentrations of DA of 100, 10, and 1 µM. The results shown in FIG. 7 indicate that the oxidation of DA molecules was detected as a clear oxidation peak for the 100 µM solution ($i_p$=0.033 µA and E=0.007 µA and E=0.164 V). Unfortunately, although the detection of the neurotransmitter was almost imperceptible in the 1 µM solution, the results shown in FIG. 7 are very promising given the simplicity of the electrode. Therefore, it should be emphasized that the limit for the electromechanical detection of DA in sophisticated 3-layer films made from PEDOT (outer and inner layer) and poly(N-methylpyrrole) (intermediate layer to create a dielectric effect) coated with AuNPs on the outer layer was 2 µM, whereas the limit in a GCE coated with a CP particularly designed to detect DA, i.e., poly(hydroxymethyl-3,4-ethylenedioxythiophene), was slightly higher.

Figure 8:
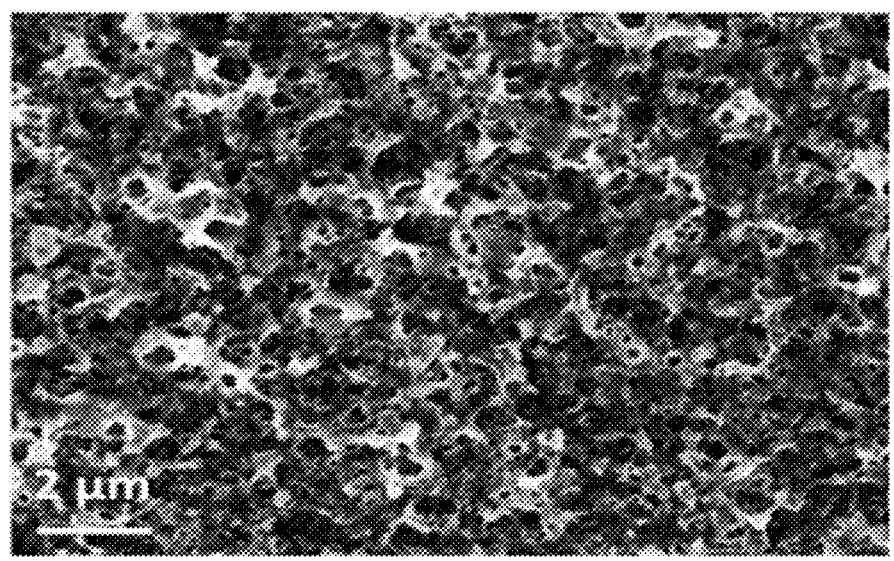
FIG. 8. Micrograph obtained by means of scanning electron microscopy (SEM) of PEDOT-coated GCE not treated with plasma.
Figure 9:
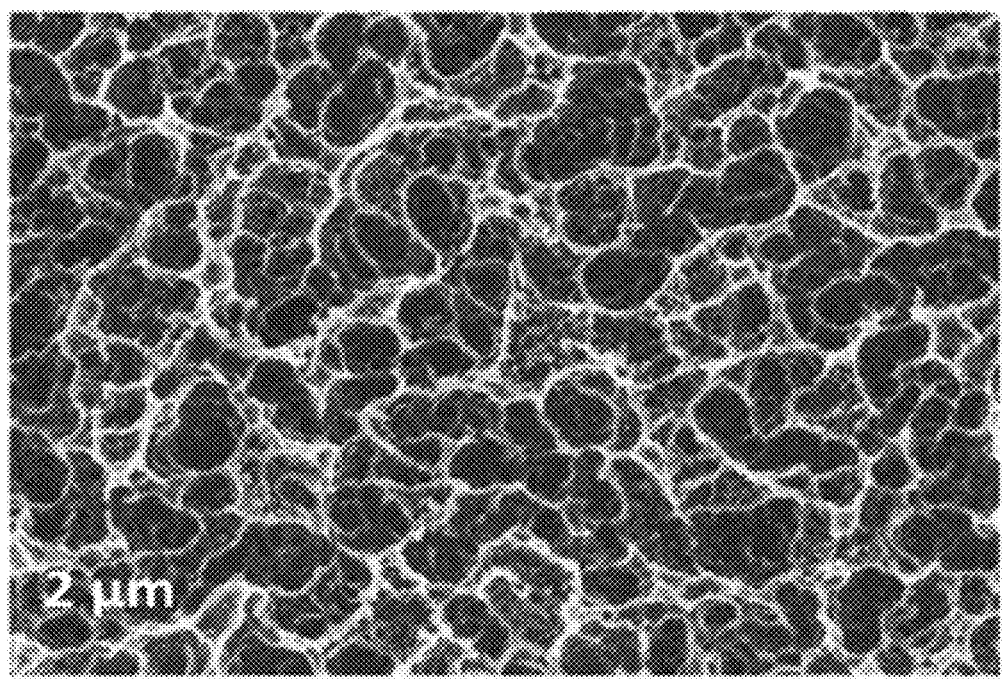
FIG. 9. SEM micrograph of the PEDOT-coated GCE treated with plasma.
Figure 10:
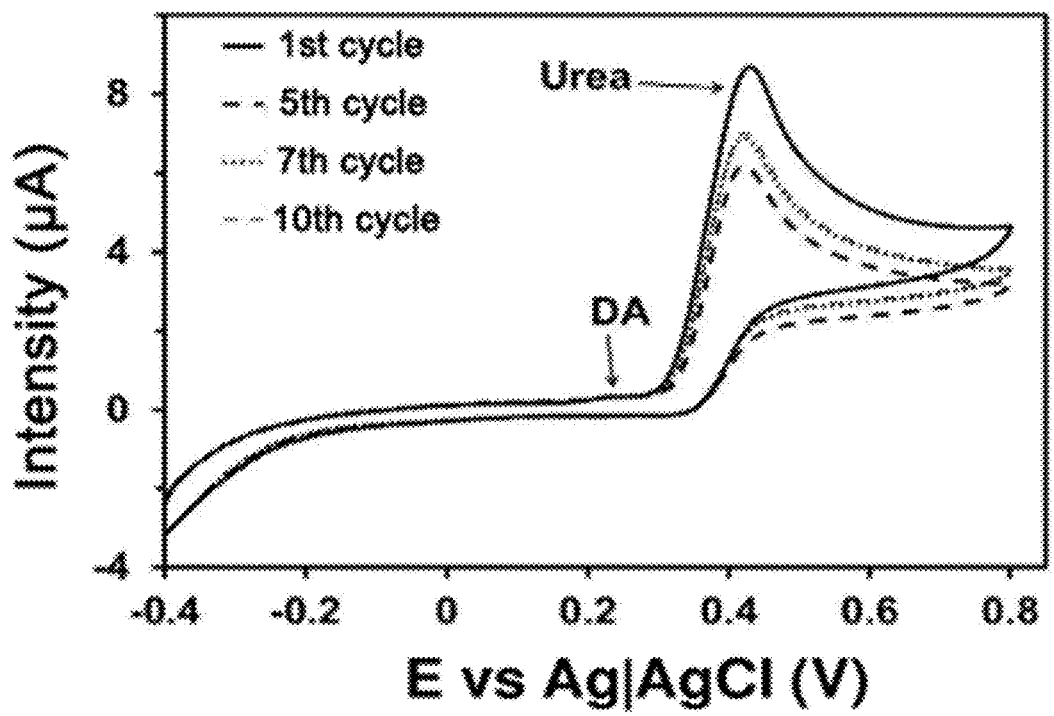
FIG. 10. Cyclic voltammetries of 10 μM dopamine in a urine-like chemical using an LDPE-coated GCE treated with plasma-air.

The surface of PEDOT-coated GCEs treated and untreated with plasma was examined using a scanning electron microscope (SEM) and energy dispersive X-ray spectroscopy (EDX). FIGS. 8 and 9 show the SEM micrographs of the PEDOT-coated GCE that is not treated and treated with plasma, respectively. The relatively compact morphology of the untreated samples (FIG. 8) which contains C, S, O, and Cl (chlorine is due to perchlorate dopant) transforms into a highly porous network of active species made up only of C and O (FIG. 10). Therefore, the electrochemical activity of polymer-coated GCEs treated with plasma could probably be attributed essentially to the surface incorporation of active species, which are possibly responsible for the detection of oxidized and reduced analytes. Similar characteristics have been observed in LDPE-coated GCEs.

Part Three

1. GCE-LDPE with Plasma: Stability and Detection of 10 µM DA in a Urine-Like Chemical The pH of the urine-like chemical is 6.2, and the chemical composition is indicated below:

| Component | mM |
|---|---|
| Urea | 200 |
| Uric acid | 1 |
| $Na_3C_6H_5O_7$ | 5 |
| NaCl | 54 |
| KCl | 30 |
| $NH_4Cl$ | 15 |
| $CaCl_2$ | 3 |
| $MgSO_4$ | 2 |
| $NaHCO_3$ | 2 |
| $Na_2C_2O_4$ | 0.1 |
| $Na_2SO_4$ | 9 |
| $KH_2PO_4$ | 3.6 |
| $Na_2HPO_4$ | 0.4 |
| $FeSO_4$ | 0.005 |
| Lactic acid | 1 |

Figure 11:
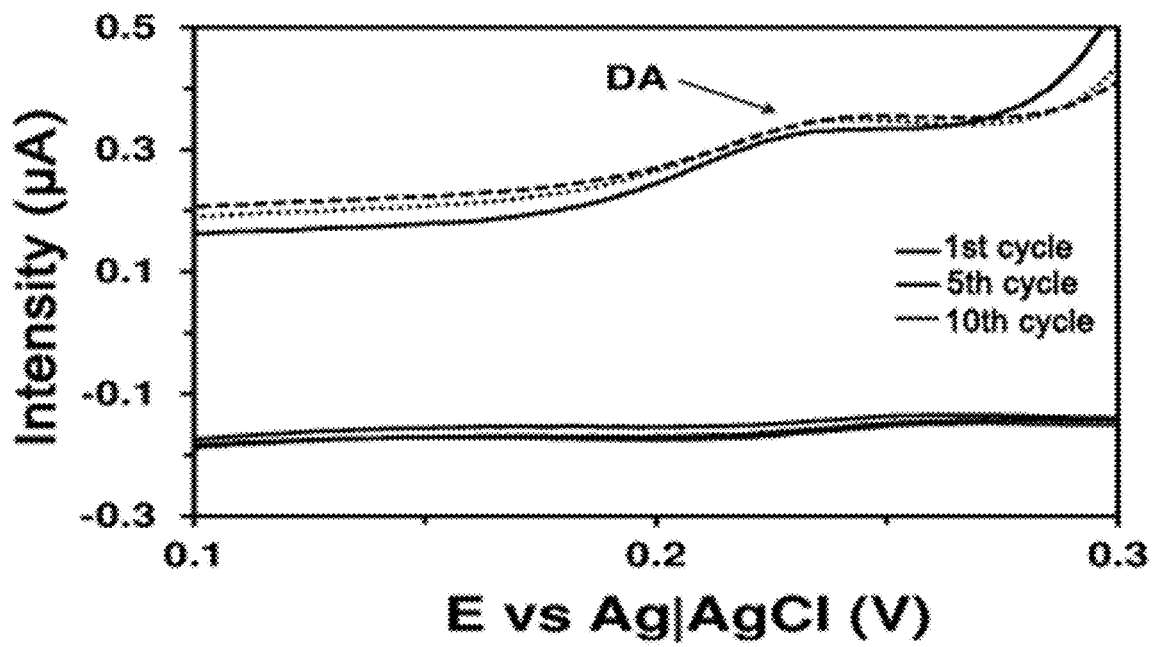
FIG. 11. Enlargement of the cyclic voltammetries in the area of oxidation of 10 μM dopamine in a urine-like chemical using an LDPE-coated GCE treated with plasma-air.

FIG. 11 shows the enlargement of the cyclic voltammetries in the area of oxidation of 10 µM dopamine in a urine-like chemical using an LDPE-coated GCE treated with plasma-air. FIG. 10 shows the cyclic voltammetries in the complete scan. The oxidation potential of dopamine is between 0.230-0.237 V, whereas the oxidation peak of urea and other components is at 0.418-0.425 V.

Figure 12:
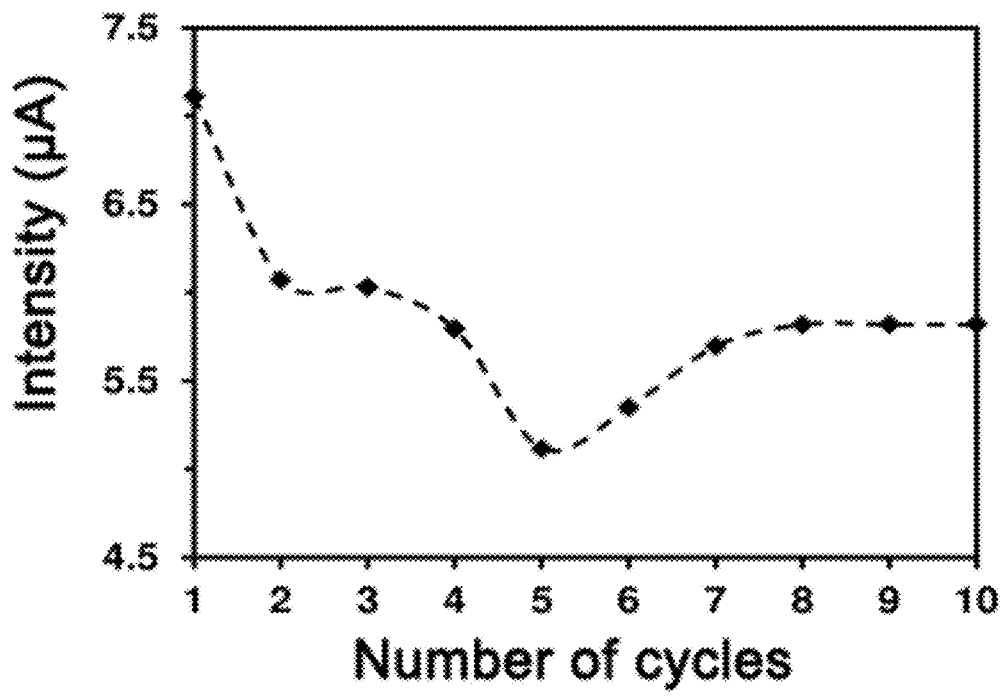
FIG. 12. Oxidation peak intensity of urea with respect to oxidation and reduction cycles in a urine-like chemical using an LDPE-coated GCE treated with plasma-air.

FIG. 12 shows the oxidation peak intensity of urea and other compounds with respect to oxidation and reduction cycles in a urine-like chemical using an LDPE-coated GCE treated with plasma-air. The oxidation potential of urea and other compounds is between 0.418 and 0.425 V. The total cycles applied to the system are 10. The intensity loss after 10 oxidation/reduction cycles is about 18%.

Figure 13:
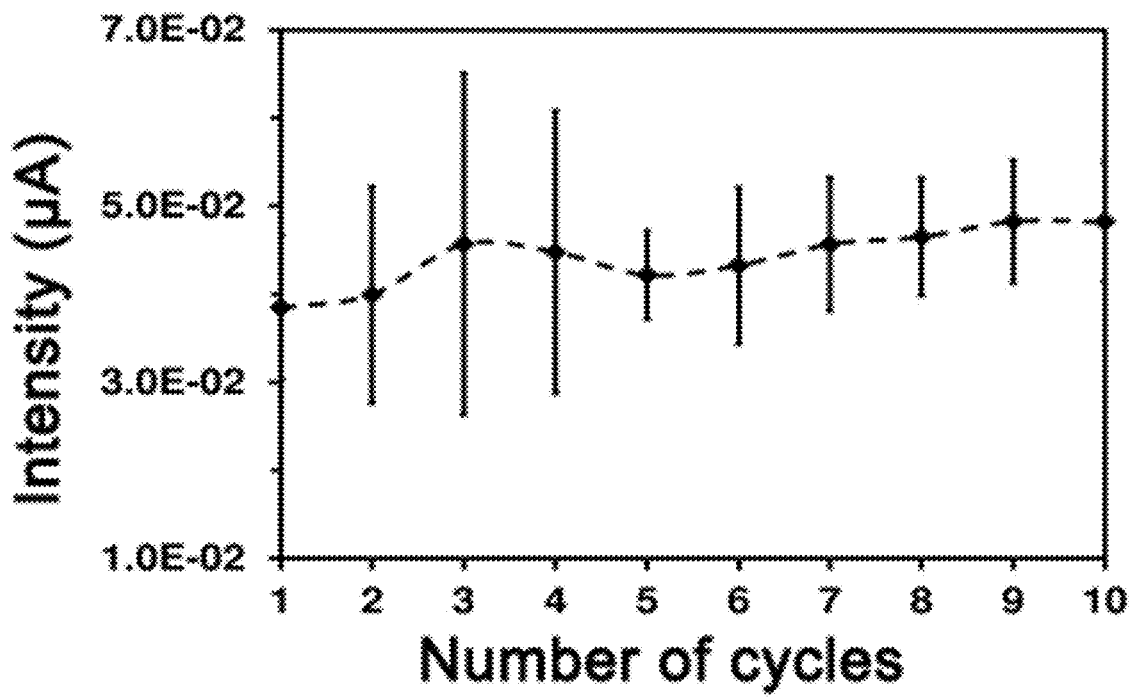
FIG. 13. Oxidation peak intensity of dopamine with respect to oxidation and reduction cycles in a urine-like chemical using an LDPE-coated GCE treated with plasma-air.

FIG. 13 shows the oxidation peak intensity of dopamine with respect to oxidation and reduction cycles in a urine-like chemical using an LDPE-coated GCE treated with plasma-air. The oxidation potential of dopamine is between 0.230 and 0.237 V. The total cycles applied to the system are 10. In this case, there is no intensity loss but there is indeed an increase of 25% after applying 10 oxidation/reduction cycles.

2. GCE-LDPE with Plasma: Stability and Detection of 10 µM DA in PBS

Figure 14:
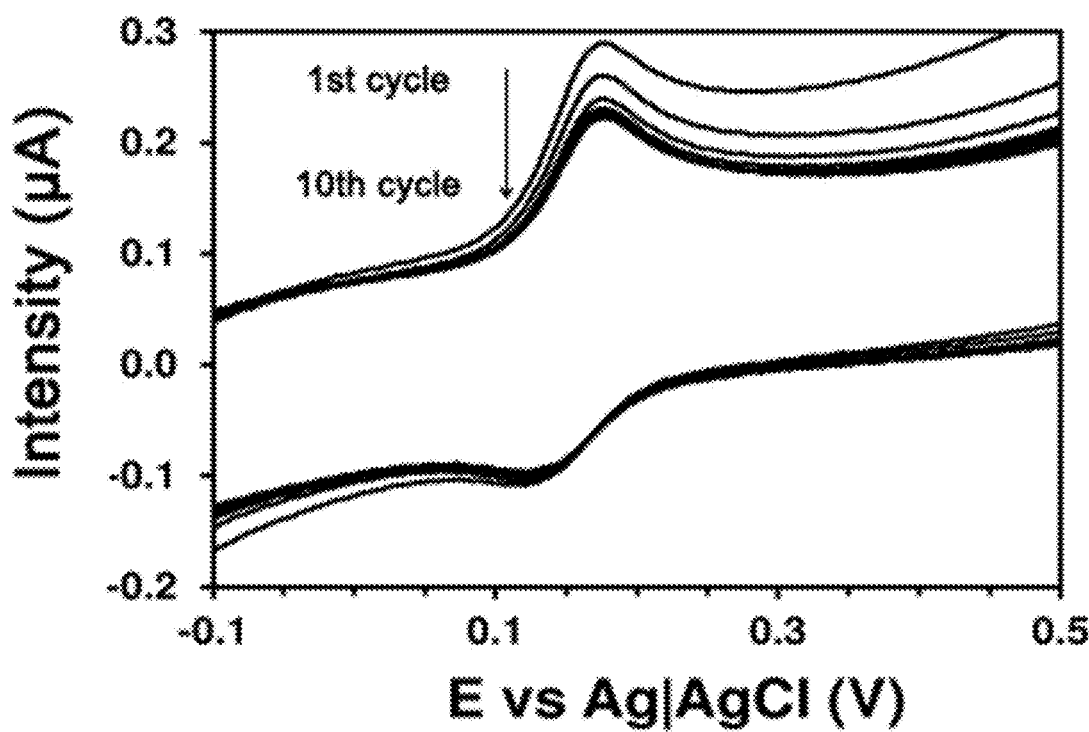
FIG. 14. Enlargement of the cyclic voltammetries in the area of oxidation of 10 μM DA in 0.1 M PBS (phosphate-buffered saline, pH 7.2) using an LDPE-coated GCE treated with plasma-air.

FIG. 14 shows the enlargement of the cyclic voltammetries in the area of oxidation of 10 µM dopamine in 0.1 M PBS (phosphate-buffered saline, pH 7.2) using an LDPE-coated GCE treated with plasma-air. The inserted box shows the cyclic voltammetries in the complete scan. The oxidation potential of dopamine is between 0.171 and 0.174 V.

Figure 15:
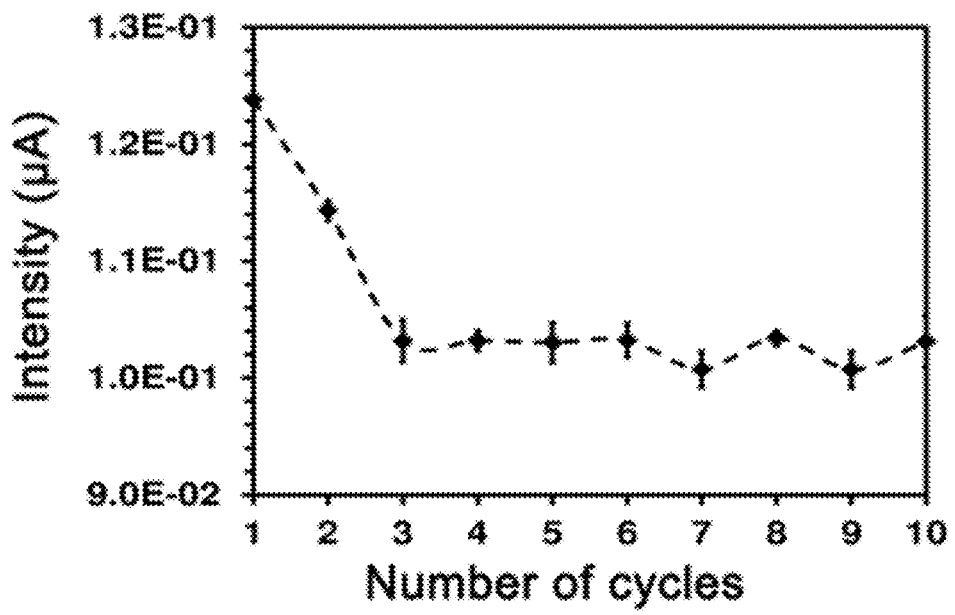
FIG. 15. Oxidation peak intensity of DA with respect to oxidation and reduction cycles in 0.1 M PBS (phosphate-buffered saline, pH 7.2) using an LDPE-coated GCE treated with plasma-air.
Figure 16:
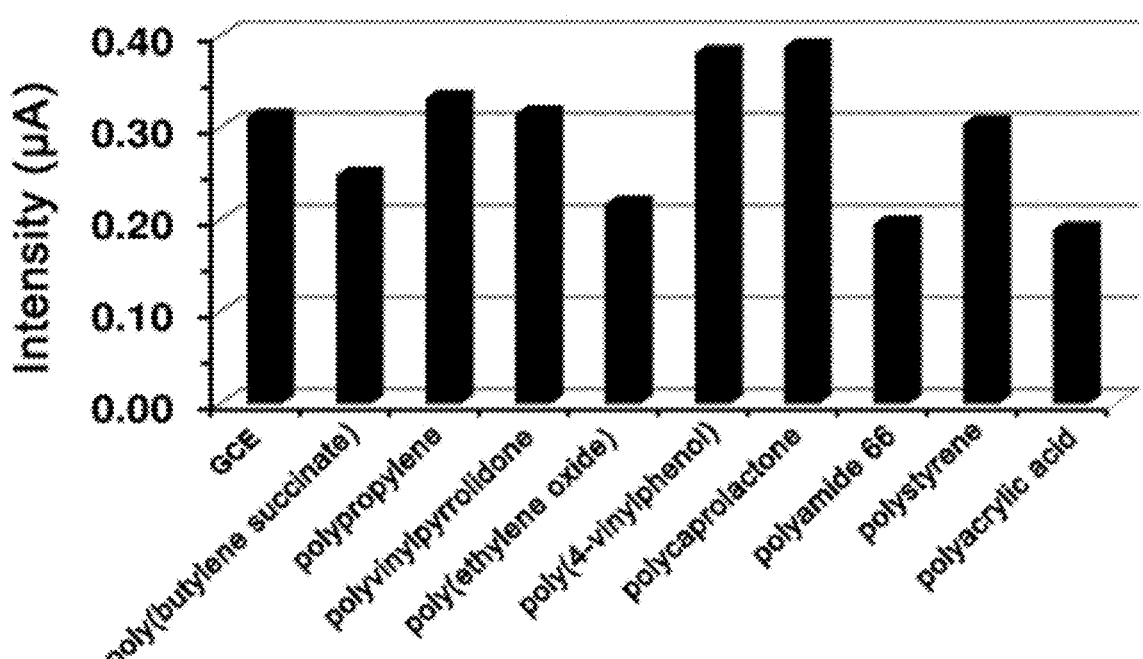
FIG. 16: Absolute intensity and peak intensity of DA using GCE coated with conventional polymer and treated with plasma-air.
Figure 17:
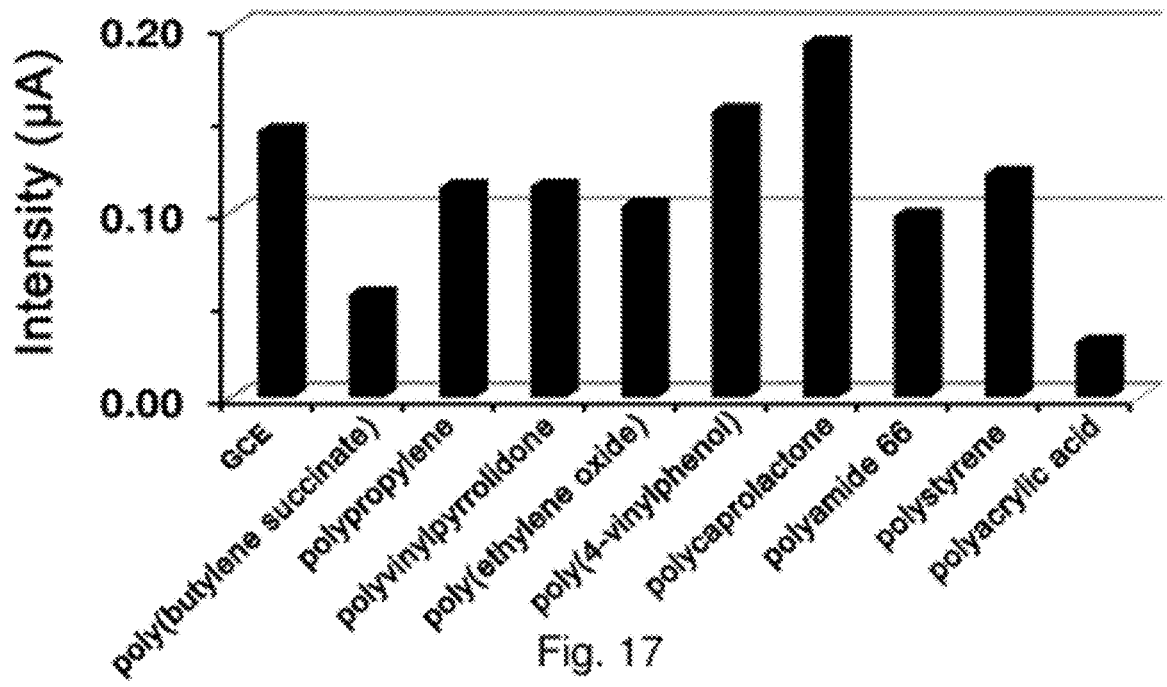
FIG. 17. Oxidation peak intensity of DA using GCE coated with conventional polymer and treated with plasma-air.
Figure 18:
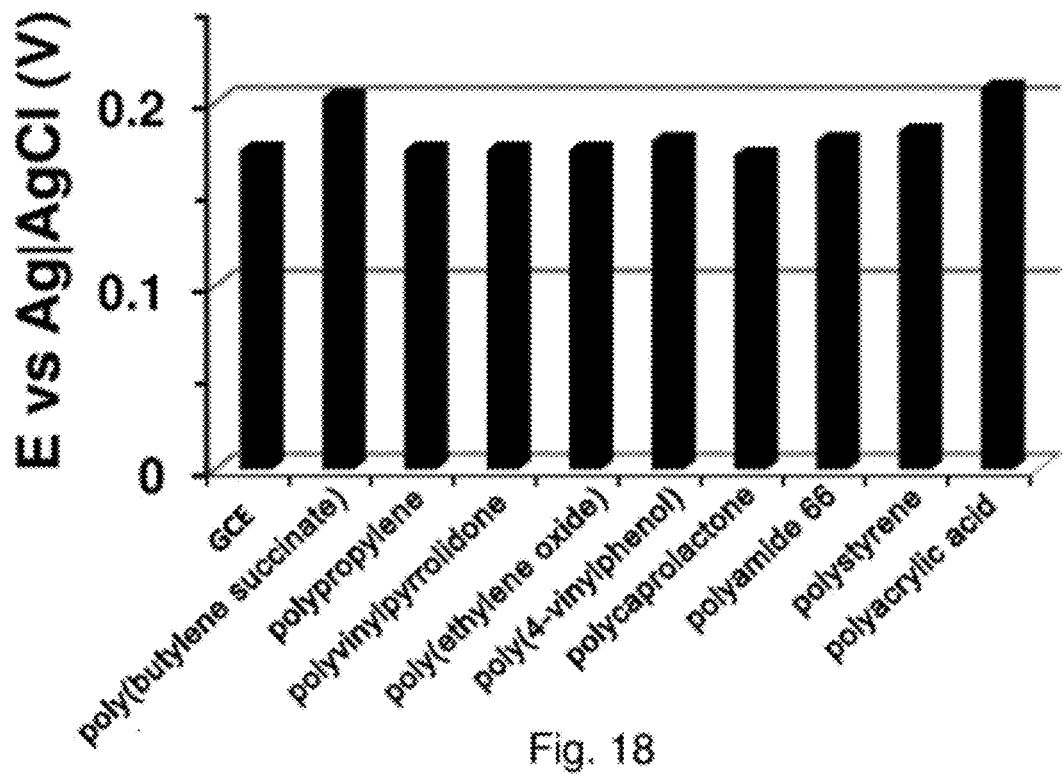
FIG. 18. Oxidation potential of DA using GCE coated with conventional polymer and treated with plasma-air.
Figure 19:
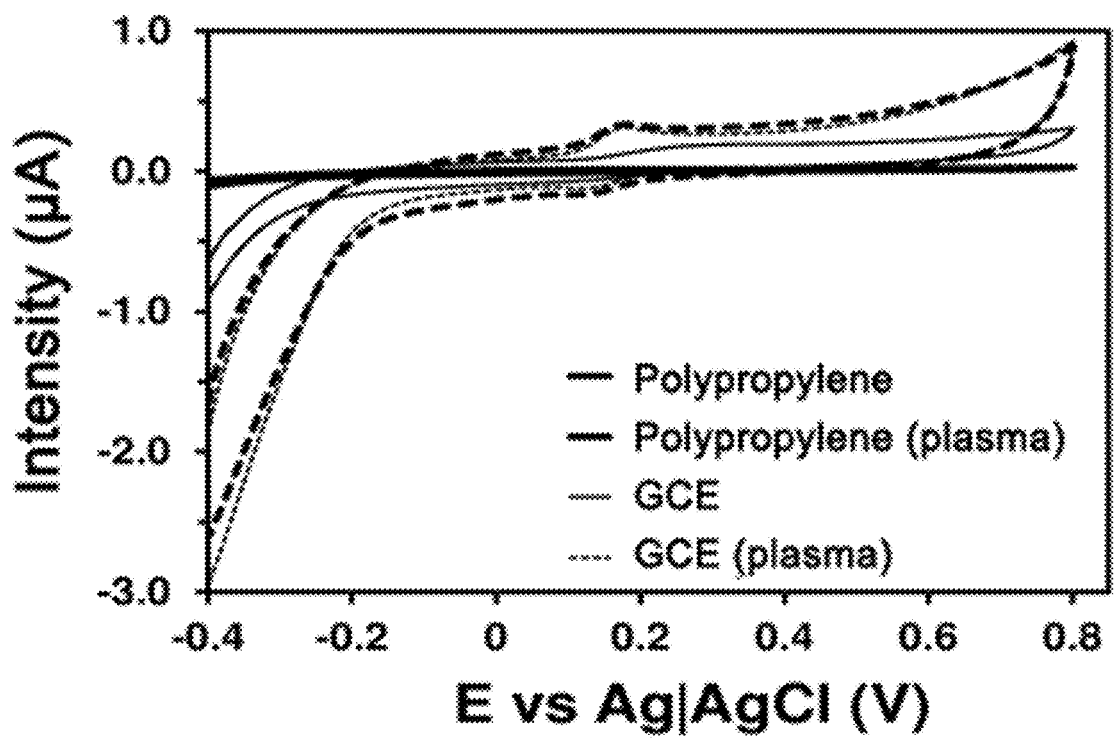
FIG. 19. Cyclic voltammetry of the oxidation of 10 μM DA in 0.1 M PBS (phosphate-buffered saline, pH 7.2) using an isotactic polypropylene-coated GCE treated with and without plasma-air. The results are compared with GCE treated with and without plasma-air.
Figure 20:
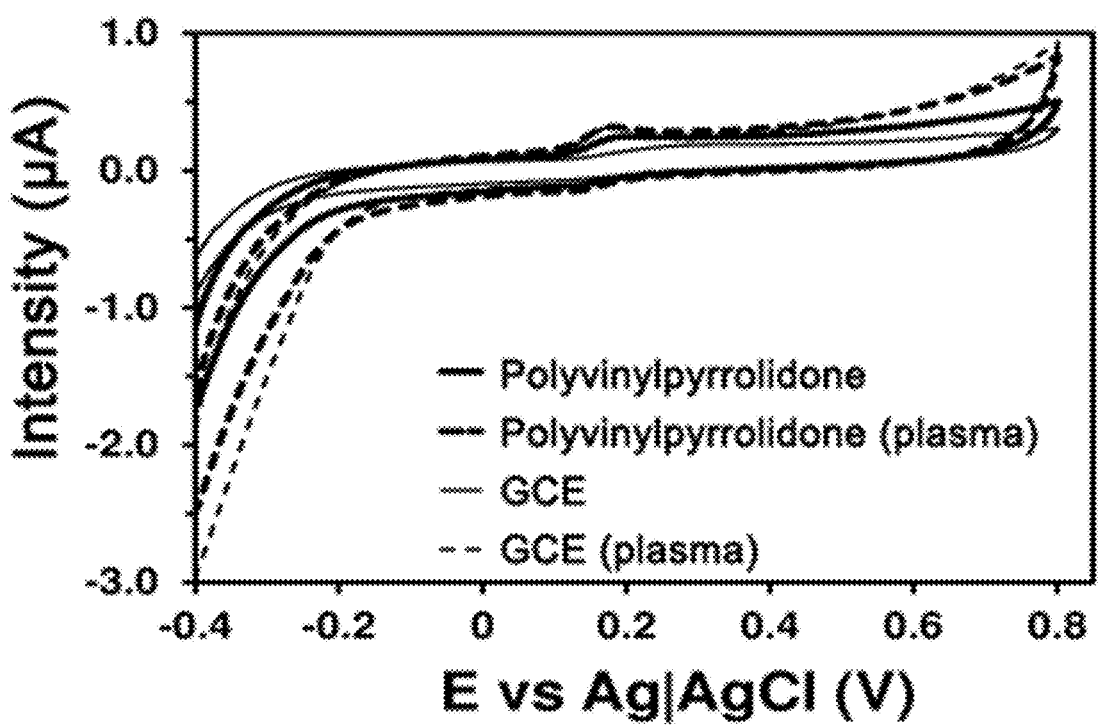
FIG. 20. Cyclic voltammetry of the oxidation of 10 μM DA in 0.1 M PBS (phosphate-buffered saline, pH 7.2) using a polyvinylpyrrolidone-treated (approximate mean molecular weight: 40,000) GCE treated with and without plasma-air. The results are compared with GCE treated with and without plasma-air.
Figure 21:
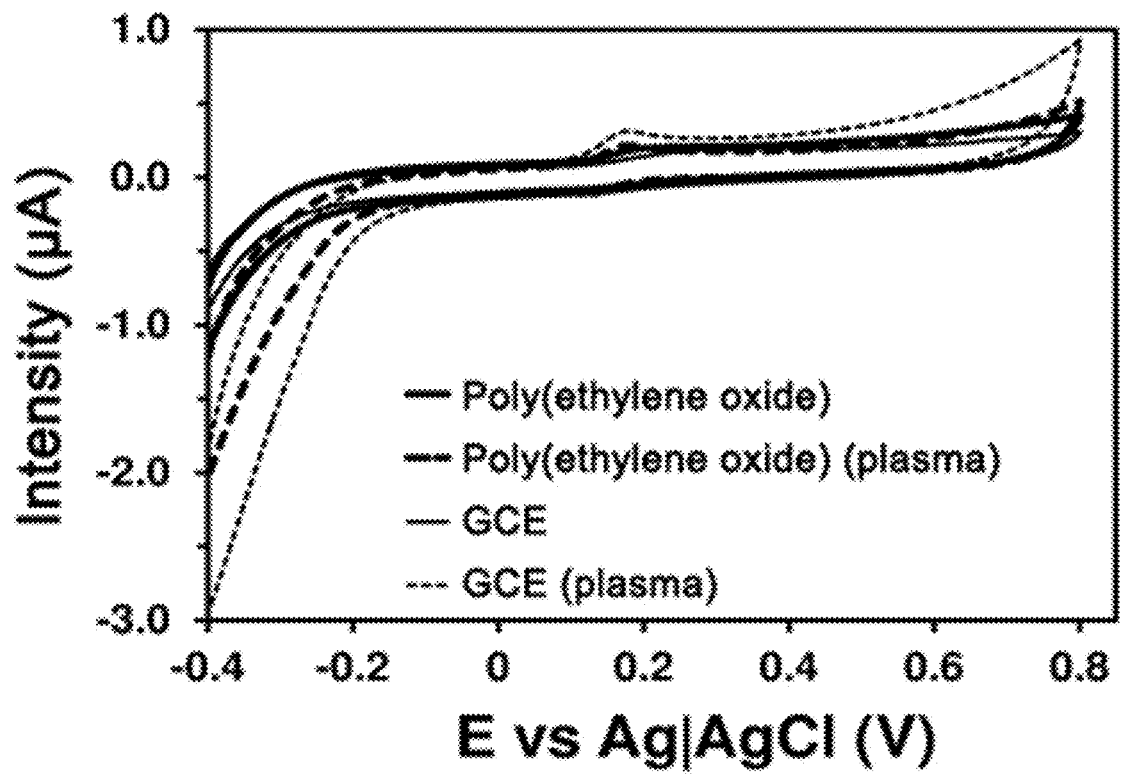
FIG. 21. Cyclic voltammetry of the oxidation of 10 μM DA in 0.1 M PBS (phosphate-buffered saline, pH 7.2) using a poly(ethylene oxide)-coated (approximate mean molecular weight: 600,000) GCE treated with and without plasma-air. The results are compared with GCE treated with and without plasma-air.
Figure 22:
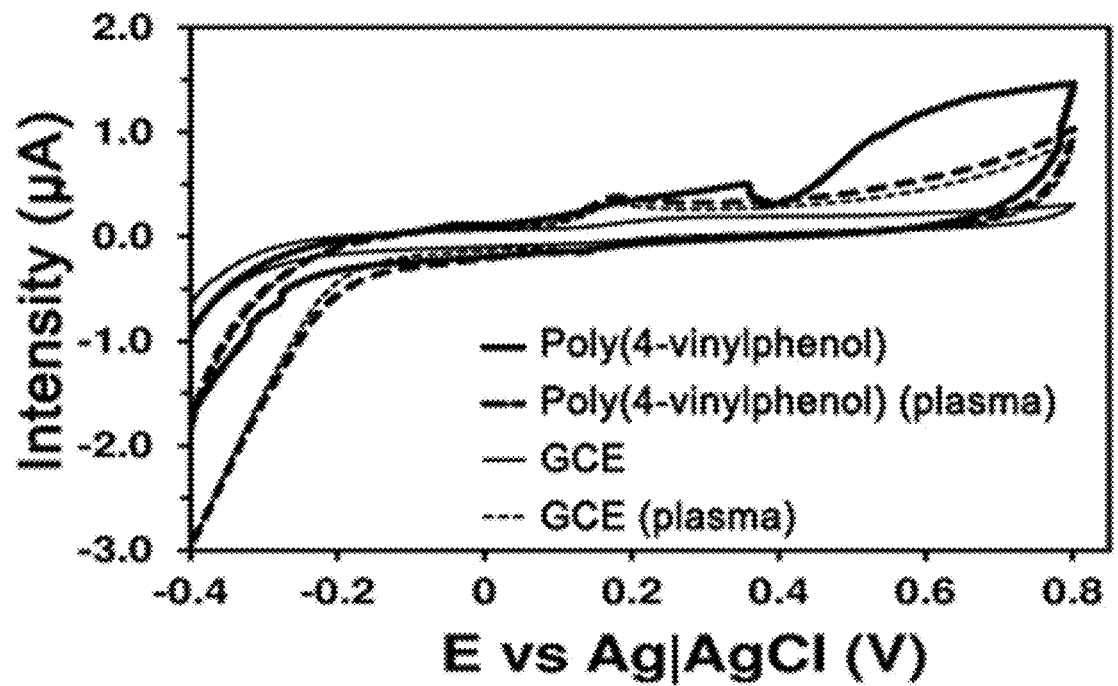
FIG. 22. Cyclic voltammetry of the oxidation of 10 μM DA in 0.1 M PBS (phosphate-buffered saline, pH 7.2) using a poly(4-vinylphenol)-coated (approximate mean molecular weight: 25,000) GCE treated with and without plasma-air. The results are compared with GCE treated with and without plasma-air.
Figure 23:
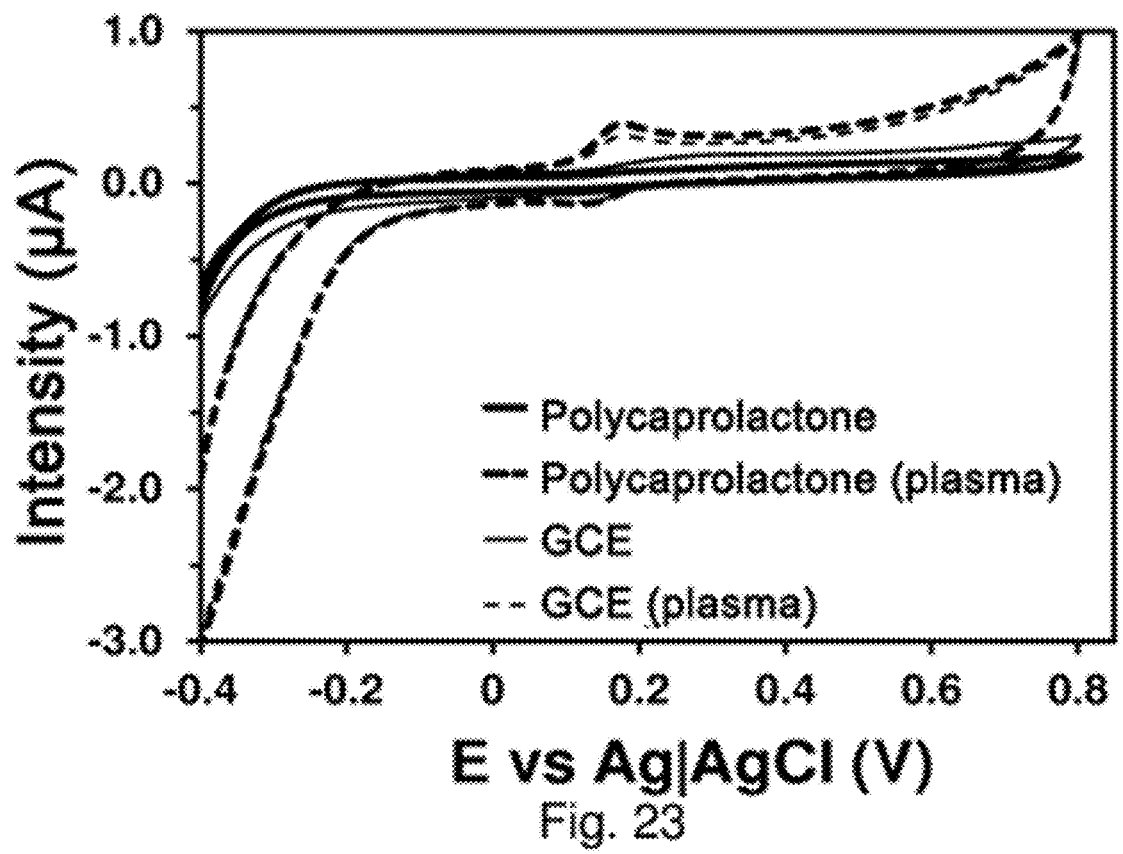
FIG. 23. Cyclic voltammetry of the oxidation of 10 μM DA in 0.1 M PBS (phosphate-buffered saline, pH 7.2) using a polycaprolactone-coated (approximate mean molecular weight: 7,000) GCE treated with and without plasma-air. The results are compared with GCE treated with and without plasma-air.
Figure 24:
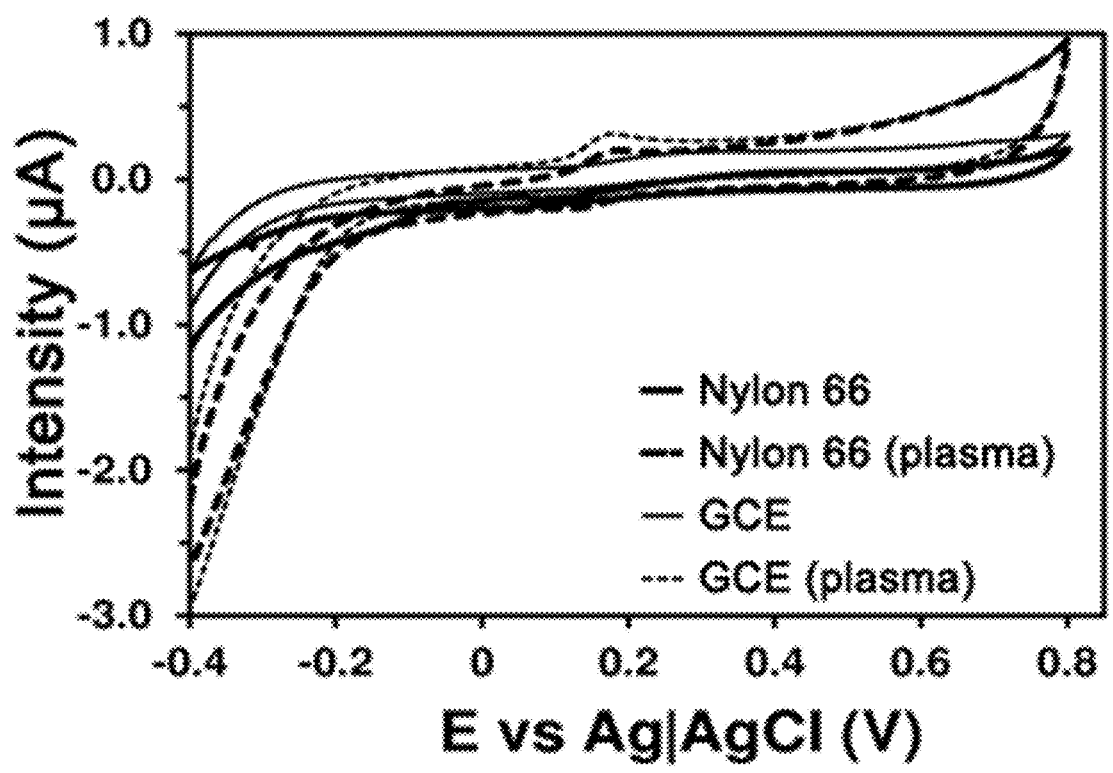
FIG. 24. Cyclic voltammetry of the oxidation of 10 μM DA in 0.1 M PBS (phosphate-buffered saline, pH 7.2) using a nylon 66 (polyamide PA 66)-coated GCE treated with and without plasma-air. The results are compared with GCE treated with and without plasma-air.
Figure 25:
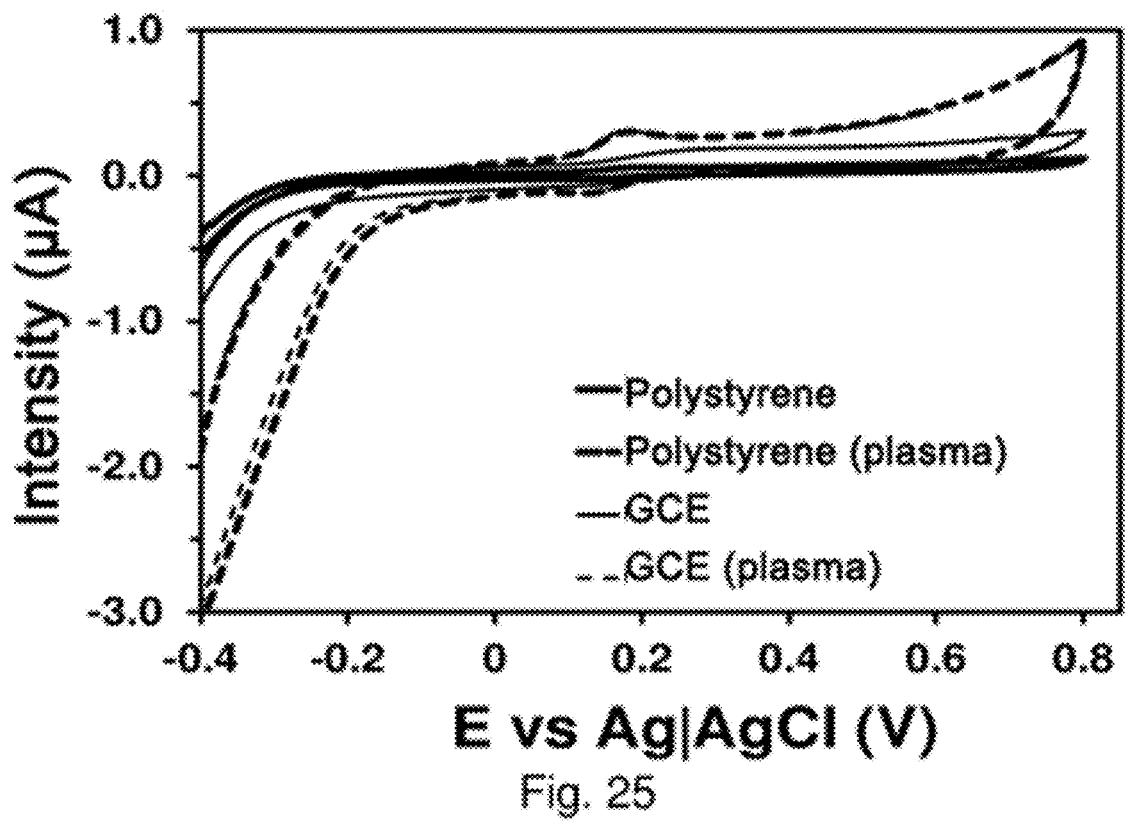
FIG. 25. Cyclic voltammetry of the oxidation of 10 μM DA in 0.1 M PBS (phosphate-buffered saline, pH 7.2) using a polystyrene-coated (from the manufacturer, Polymer Additives) GCE treated with and without plasma-air. The results are compared with GCE treated with and without plasma-air.
Figure 26:
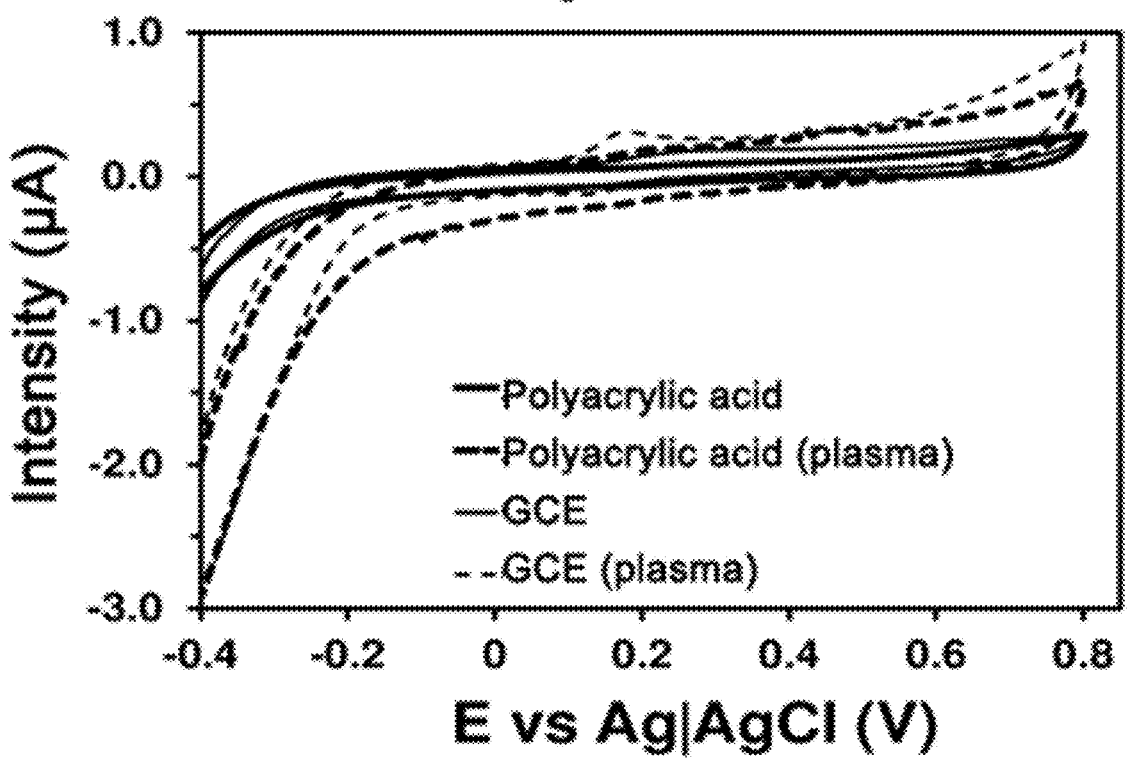
FIG. 26. Cyclic voltammetry of the oxidation of 10 μM DA in 0.1 M PBS (phosphate-buffered saline, pH 7.2) using a polyacrylic acid-coated (25% by weight in water, approximate mean molecular weight: 240,000) GCE treated with and without plasma-air. The results are compared with GCE treated with and without plasma-air.
Figure 27:
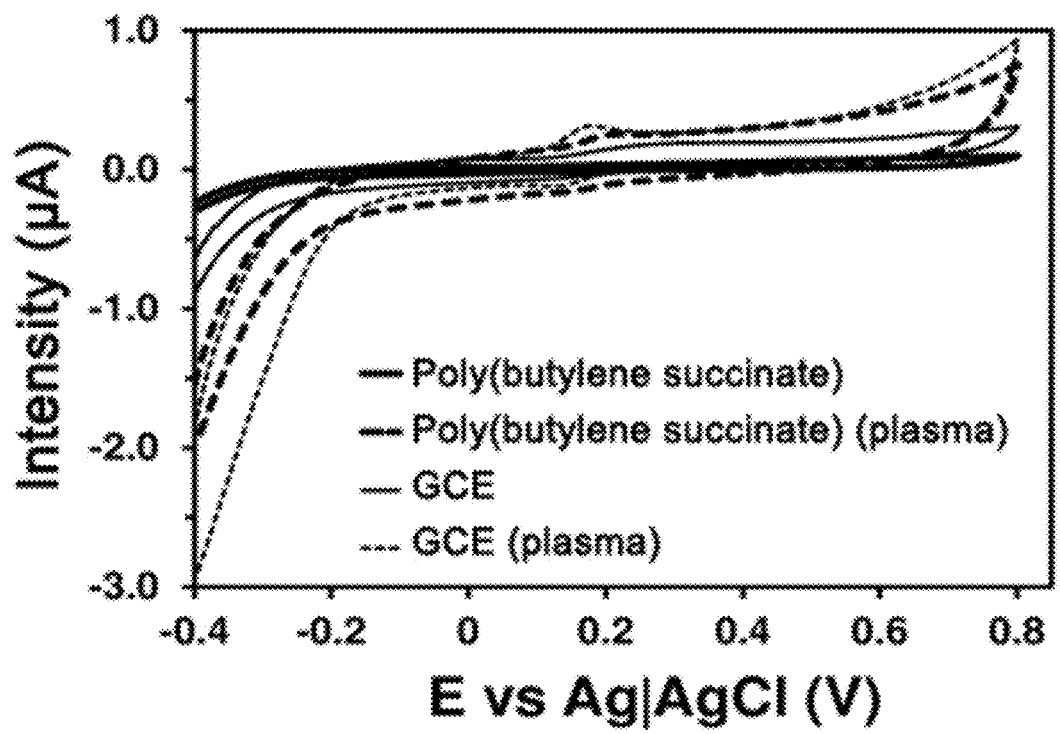
FIG. 27. Cyclic voltammetry of the oxidation of 10 μM DA in 0.1 M PBS (phosphate-buffered saline, pH 7.2) using a poly(butylene succinate)-coated (sold under the brand name Bionolle®) GCE treated with and without plasma-air. The results are compared with GCE treated with and without plasma-air.
Figure 28:
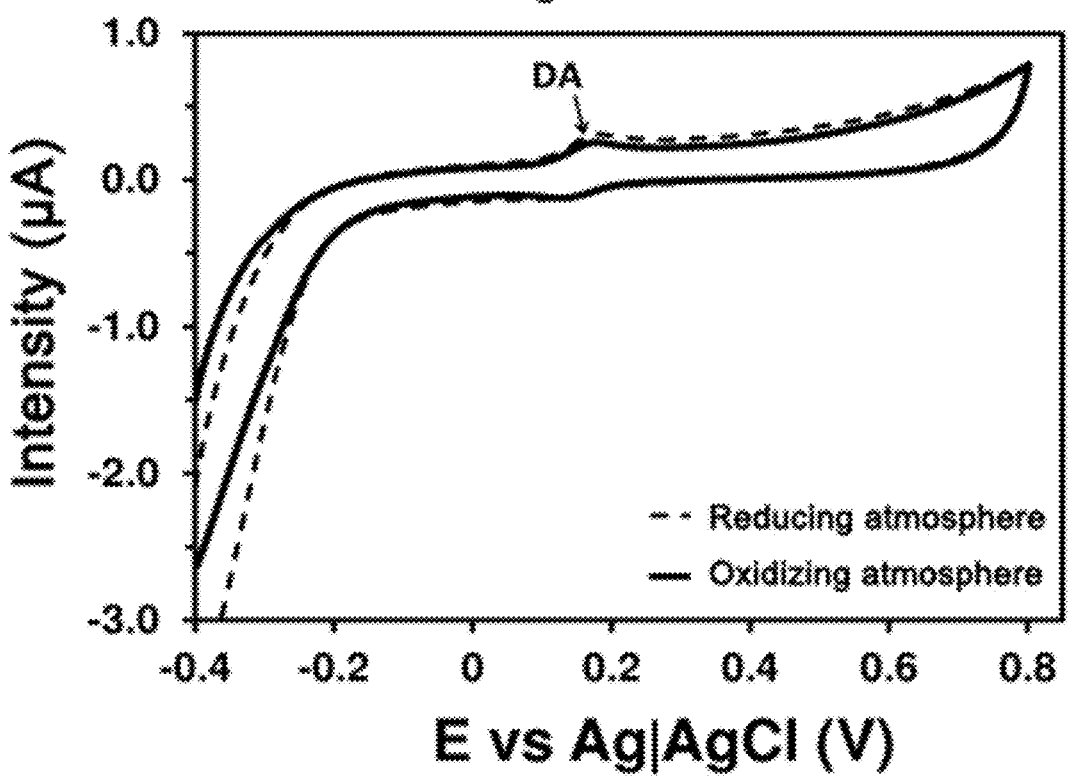
FIG. 28. Cyclic voltammetry of the oxidation of 10 μM DA in 0.1 M PBS (phosphate-buffered saline, pH 7.2) using an LDPE-coated GCE treated with cold plasma in oxidizing and reducing atmosphere.

FIG. 15 shows the oxidation peak intensity of dopamine with respect to oxidation and reduction cycles in 0.1 M PBS (phosphate-buffered saline, pH 7.2) using an LDPE-coated GCE treated with plasma-air. The oxidation potential of dopamine is between 0.171 and 0.174 V. The total cycles applied to the system are 10. The intensity loss after 10 oxidation/reduction cycles is about 17%.

3. Alternative Substrates with Polyethylene

Inorganic base substrates, i.e., substrates not rich in carbon (i.e., with less than 50% by weight of carbon with respect to the total weight of the substrate) have been tested. Specifically, ITO (indium tin oxide) substrate and AISI 316 stainless steel substrate have been tested, coated in both cases with a low-density polyethylene. In both cases, the substrates are negatively affected by plasma application and favorable results are not obtained.

4. Alternative Polymers

Other conventional polymers applied on a GCE not treated and treated with plasma under the same conditions as LDPE have been assayed for the detection of 10 µM DA in PBS. The following table shows the assayed polymers, the solvent and amount of polymer used in the preparation of the film being indicated.

| POLYMER | SOLVENT | AMOUNT OF POLYMER (MG) |
|---|---|---|
| <br>Isotactic polypropylene | o-dichlorobenzene, 10 ml | 52.4 |
| 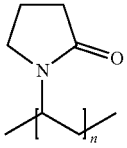<br>Polyvinylpyrrolidone | chloroform, 10 ml | 43 |
| 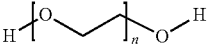<br>Poly(ethylene oxide) | chloroform, 10 ml | 43.6 |
| 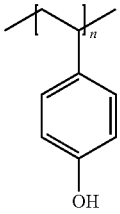<br>Poly(4-vinylphenol) | methanol, 4 ml | 11.8 |
| 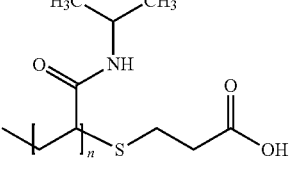<br>Polycaprolactone | chloroform, 10 ml | 46.5 |
| 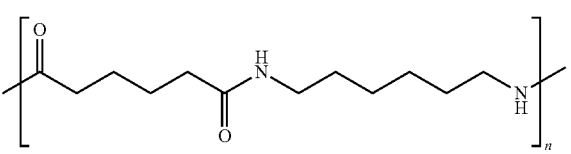<br>Nylon 66 | hydrochloric acid, 10 ml | 43.5 |

| POLYMER | SOLVENT | AMOUNT OF POLYMER (MG) |
|---|---|---|
| Polystyrene | chloroform, 10 ml | 33.5 |
| Polyacrylic acid | water | 25 wt % |
| poly(butylene succinate) | chloroform/ dichloromethane (50/50), 10 ml | 47.6 |

The following table shows the intensities, Iabs (absolute, without baseline), and Ipeak (with baseline), and the oxidation potential obtained in the detection of 10 μM dopamine in 0.1 M PBS for GCE coated with conventional polymer and treated with cold plasma (oxidizing atmosphere).

| | 10 μM dopamine | | |
|---|---|---|---|
| PLASMA | Ipeak (μA) | Iabs (μA) | Eox (V) |
| GCE - plasma | 1.44E−01 | 3.12E−01 | 0.174 |
| Poly(butylene succinate) - plasma | 5.57E−02 | 2.49E−01 | 0.203 |
| Polypropylene - plasma | 1.14E−01 | 3.32E−01 | 0.174 |
| Polyvinylpyrrolidone - plasma | 1.14E−01 | 3.15E−01 | 0.174 |
| Poly(ethylene oxide) - plasma | 1.04E−01 | 2.17E−01 | 0.174 |
| Poly(4-vinylphenol) - plasma | 1.55E−01 | 3.81E−01 | 0.179 |
| Polycaprolactone - plasma | 1.91E−01 | 3.88E−01 | 0.171 |
| Nylon 66 - plasma | 9.81E−02 | 1.96E−01 | 0.179 |
| Polystyrene - plasma | 1.21E−01 | 3.05E−01 | 0.184 |
| Polyacrylic acid - plasma | 2.99E−02 | 1.89E−01 | 0.208 |

FIGS. 16 to 27 show the results that are obtained. As can be seen, the application of plasma-air on other conventional polymers produces effects similar to those obtained with LDPE.

5. Non-Oxidizing Atmosphere

Assays have been performed with non-oxidizing atmospheres, specifically with $N_2$ atmosphere, with LDPE-coated GCE obtained according to the preceding conditions.

Figure 29:
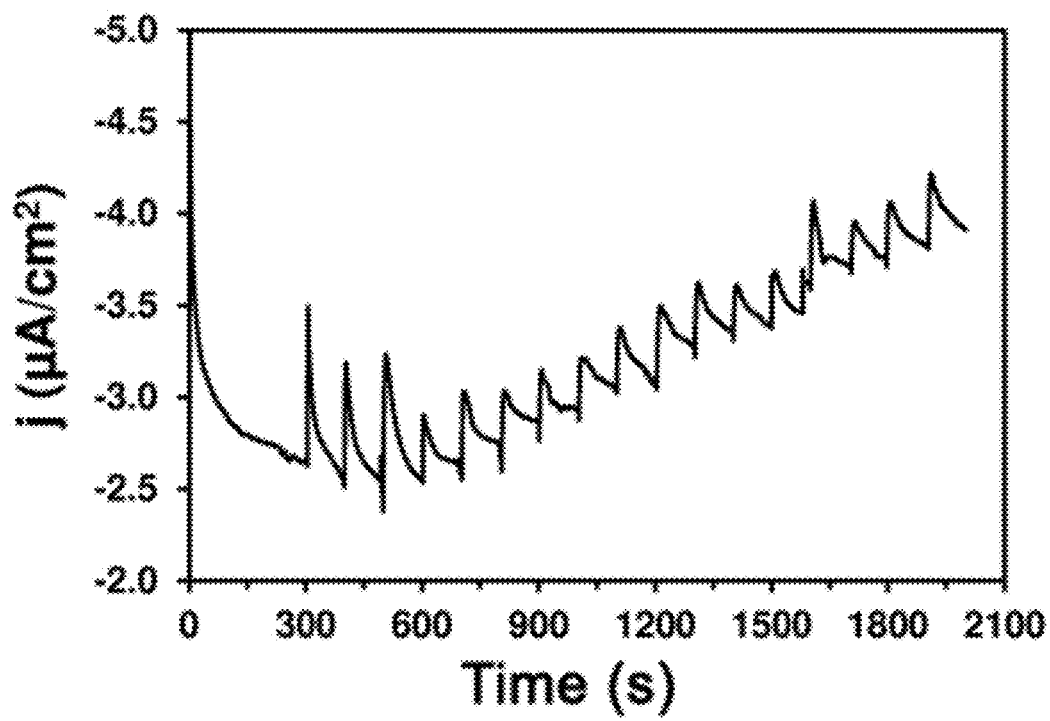
FIG. 29. Current vs. time density graph for the chronoamperometric detection of 1 mM glucose using a PEDOT-coated GCE treated with plasma-air on which the glucose oxidase enzyme has been immobilized. Injection of glucose into the detection cell starts at 300 s and is performed every 100 s.

The results that are obtained are shown in FIG. 29 and in the following table:

| | Oxidizing atmosphere | Non-oxidizing atmosphere |
|---|---|---|
| Oxidation potential (V) | 0.174 | 0.171 |
| Peak intensity (μA) | 2.03E−1 | 1.09E−1 |
| Absolute intensity (μA) | 6.27E−1 | 6E−1 |

As can be seen, the use of non-oxidizing atmosphere in the application of cold plasma produces effects similar to those described with oxidizing atmosphere.

Part Four

Monitoring glucose levels in the human body is fundamental for the diagnosis and treatment of diabetes which has become a public health problem worldwide. Furthermore, monitoring glucose metabolism through the detection of changes in the concentration of this analyte can improve the treatment of brain diseases, such as, for example, tumors and brain injuries. The detection of glucose is also very important in the food processing, fermentation, and bio-fuel cell industry.

Another surprising result of the present invention is the preparation of electrochemical glucose sensors by means of applying cold plasma surface treatment (corona plasma in ambient atmosphere at about 0.5 J/cm² for 2 minutes) to polymer films deposited on a CGE.

The selective and simultaneous detection of DA, UA (uric acid), and AA (ascorbic acid) using PNCPy is difficult because the oxidation peaks of each of these organic substances are weak and partially overlap one another, whereas, in contrast, the oxidation peaks are well resolved when PEDOT-coated electrodes are used. The behavior of PNMPy improves when the film is covered with gold nanoparticles (AuNPs), which demonstrates the electrocatalytic activity that the latter promote. In contrast, the properties of the PEDOT electrodes for the selective detection of DA remain virtually unchanged after the incorporation of AuNPs.

Figure 30:
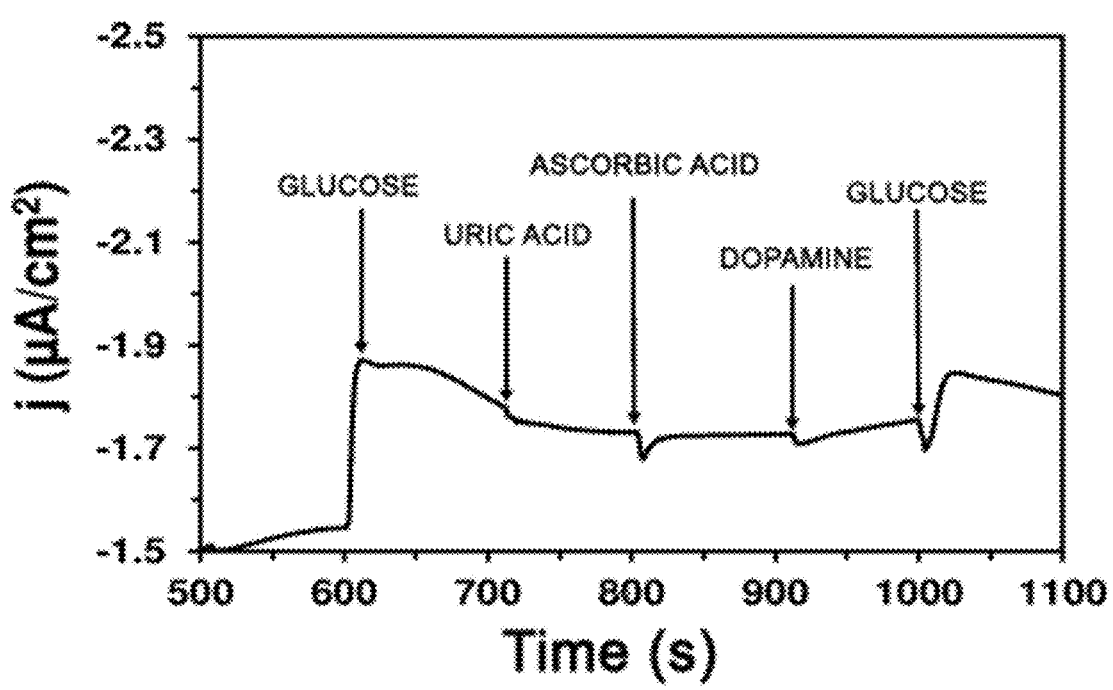
FIG. 30. Current vs. time density graph for the chronoamperometric detection of 1 mM glucose, 1 mM UA, 1 mM AA, and 1 mM DA using a PEDOT-coated GCE treated with plasma-air on which the glucose oxidase enzyme has been immobilized. Injection of glucose and different interfering substances into the detection cell starts at 500 s and is performed every 100 s.
Figure 31:
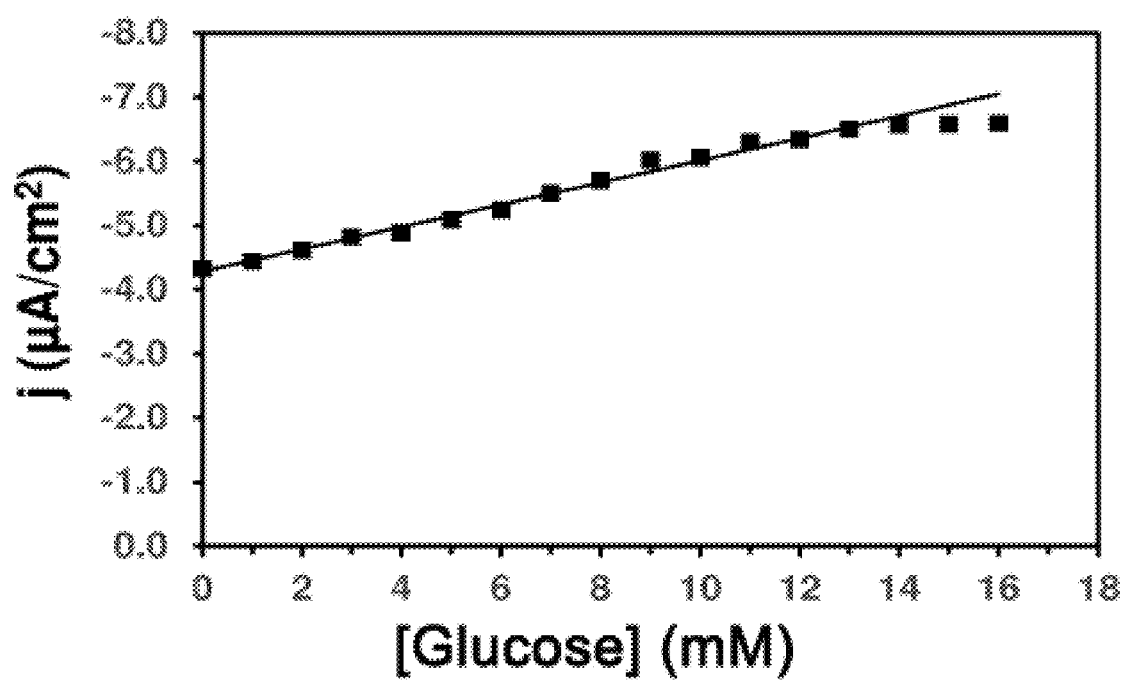
FIG. 31. Determination of the glucose detection limit of the GCE coated with PEDOT and with a plasma-air treatment. The glucose oxidase enzyme was immobilized on the surface of the electrode.

Both the PEDOT films and the PNCPy films generated by anodic polymerization on a CGE electrode were modified by means of applying cold plasma surface treatment (corona plasma in ambient atmosphere at about 0.5 J/cm$^2$ for 2 minutes). Glucose detection assays in the absence and presence of interfering substances (1 mM DA, UA, and AA) were carried out by means of chronoamperometry at room temperature. FIGS. 29 to 30 show the chronoamperometric response of the PEDOT-coated GCEs treated with plasma. As can be seen, the electrodes treated with plasma are capable of selectively detecting glucose oxidation. FIG. 31 shows the determination of the glucose detection limit of the GCE coated with PEDOT and with cold plasma treatment by means of chronoamperometry. The results were derived from successive standard injection of glucose. The detection limit which was determined using the calibration line obtained for a maximum concentration of glucose 14 mM was 1 mM.

In conclusion, several very simple methods have been described for the electrochemical detection of DA or glucose, for example. Said methods have resulted in sensors with a resolution and sensitivity similar to those achieved by means of sophisticated chemical modifications, such as, for example, the incorporation of AuNPs to CP coatings, the preparation of multilayer CP compounds, or the functionalization of monomers. Furthermore, it has been demonstrated that these new methods were a success when applied not only to CPs, but also to layers of other non-electrochemically active polymers, such as LDPE, for example. This paves the way to a quick, easy, and simple way of producing sensitive detectors, for example, DA detectors, glucose detectors, etc., which can be implemented as very cost-effective diagnostic tests.

The invention claimed is:

1. An electrochemical sensor coating method, comprising the steps of:
 coating a carbon-rich substrate of the electrochemical sensor with an organic low density polyethylene (LDPE) coating, the substrate having a carbon content greater than or equal to 50% by weight with respect to the total weight of the substrate, and
 applying a cold plasma treatment to said coating thereby converting at least a portion of the LDPE coating surface into active species of carbon and oxygen,
 wherein the carbon-rich substrate is made of a material from the group consisting of graphite, glassy carbon, nanostructured carbons, and fullerenes.

2. The method according to claim 1, wherein said plasma is an atmospheric plasma, a vacuum plasma, or a corona energy plasma comprising between 0.1 mJ/cm$^2$ and 100 J/cm$^2$ in an atmosphere with oxygen, or nitrogen, or another inert gas.

3. The method according to claim 1, wherein the plasma application time is more than 1 s.

4. The method according to claim 3, wherein the plasma application time is more than 15 s.

5. The method according to claim 1, wherein the plasma application time is less than 120 s.

6. The method of claim 1, wherein the electrochemical sensor is for detection of dopamine, glucose, uric acid or ascorbic acid.

7. The method according to claim 1, wherein the nanostructured carbons comprise graphene or carbon nanotubes.

8. A production method for producing an electrochemical sensor comprising a carbon-rich substrate with a carbon content greater than or equal to 50% by weight with respect to the total weight of the substrate, wherein the method comprises the steps of claim 1.

9. An electrochemical sensor, comprising a carbon-rich substrate having a carbon content greater than or equal to 50% by weight with respect to the total weight of the substrate, and an organic low density polyethylene (LDPE) coating deposited on the carbon-rich substrate,
 wherein said LDPE coating has been treated by a cold plasma and the treated LDPE coating comprises carbon and oxygen as active species on its surface;
 wherein the carbon-rich substrate is made of a material from the group consisting of graphite, glassy carbon, nanostructured carbons, and fullerenes.

10. A method for detecting an analyte selected from the group consisting of dopamine, glucose, uric acid, and ascorbic acid, the method comprising contacting the analyte with the electrochemical sensor of claim 9.

11. The electrochemical sensor of claim 9, wherein the electrochemical sensor is for detection of dopamine, glucose, uric acid or ascorbic acid.

12. The electrochemical sensor of claim 9, wherein cold plasma is atmospheric plasma, air plasma, oxygen plasma, or nitrogen plasma.

* * * * *